US010131633B2

United States Patent
Suzuki et al.

(10) Patent No.: US 10,131,633 B2
(45) Date of Patent: Nov. 20, 2018

(54) CATIONIC LIPID

(71) Applicants: Eisai R&D Management Co., Ltd., Tokyo (JP); Sogo Pharmaceutical Co., Ltd., Tokyo (JP)

(72) Inventors: Yuta Suzuki, Tsukuba (JP); Kenji Hyodo, Tsukuba (JP); Yohei Tanaka, Nakama (JP)

(73) Assignees: Eisai R&D Management Co., Ltd., Tokyo (JP); Sogo Pharmaceutical Co., Ltd., Tokyo (JP)

( * ) Notice: Subject to any disclaimer, the term of this patent is extended or adjusted under 35 U.S.C. 154(b) by 0 days.

(21) Appl. No.: 15/841,652

(22) Filed: Dec. 14, 2017

(65) Prior Publication Data

US 2018/0105493 A1 Apr. 19, 2018

Related U.S. Application Data

(62) Division of application No. 15/109,512, filed as application No. PCT/JP2015/050295 on Jan. 7, 2015, now Pat. No. 9,873,669.

(60) Provisional application No. 61/925,267, filed on Jan. 9, 2014.

(51) Int. Cl.

| C07D 207/16 | (2006.01) |
| C07D 211/62 | (2006.01) |
| A61K 47/22 | (2006.01) |
| A61K 9/51 | (2006.01) |
| C07D 205/04 | (2006.01) |
| C12N 15/11 | (2006.01) |
| A61K 48/00 | (2006.01) |
| C12N 15/113 | (2010.01) |

(52) U.S. Cl.
CPC .......... *C07D 211/62* (2013.01); *A61K 9/5123* (2013.01); *A61K 47/22* (2013.01); *A61K 48/0033* (2013.01); *C07D 205/04* (2013.01); *C07D 207/16* (2013.01); *C12N 15/111* (2013.01); *C12N 15/1137* (2013.01); *C12N 2310/14* (2013.01); *C12N 2320/32* (2013.01)

(58) Field of Classification Search
CPC .................................................... C07D 207/16
USPC ......................................................... 548/531
See application file for complete search history.

(56) References Cited

U.S. PATENT DOCUMENTS

| 8,158,601 B2 | 4/2012 | Chen et al. |
| 9,873,669 B2 | 1/2018 | Suzuki et al. |
| 2011/0256175 A1 | 10/2011 | Hope |
| 2013/0178541 A1 | 7/2013 | Stanton et al. |

FOREIGN PATENT DOCUMENTS

| CN | 103167866 | 6/2013 |
| JP | 2012530059 | 11/2012 |
| WO | WO 2010/042877 | 4/2010 |
| WO | WO 2010/144740 | 12/2010 |
| WO | WO 2012/040184 | 3/2012 |
| WO | WO 2013/059496 | 4/2013 |
| WO | WO 2013/158579 | 10/2013 |

OTHER PUBLICATIONS

Notice of Allowance in U.S. Appl. No. 15/109,512, dated Sep. 18, 2017, 7 pages.
Office Action in U.S. Appl. No. 15/109,512, dated May 19, 2017, 34 pages.
Restriction Requirement in U.S. Appl. No. 15/109,512, dated Mar. 13, 2017, 8 pages.
Response to Restriction Requirement in U.S. Appl. No. 15/109,512, dated May 10, 2017, 3 pages.
Response to Office Action in U.S. Appl. No. 15/109,512, dated Aug. 16, 2017, 10 pages.
Chinese Office Action in Chinese Application No. 201580003735.2, dated May 27, 2017, 10 pages. (English Abstract).
European Search Report in European Application No. 15735252.7, dated Jun. 8, 2017, 6 pages.
Gindy, M.E. et al., "Stabilization of Ostwald Ripening in Low Molecular Weight Amino Lipid Nanoparticles for Systemic Delivery of siRNA Therapeutics", *Mol. Pharmaceutics* (2014), 11:4143-4153.
International Search Report issued in International Application No. PCT/JP2015/050295, dated Feb. 17, 2015, with English Translation.
Jayaraman, M. et al., "Maximizing the Potency of siRNA Lipid Nanoparticles for Hepatic Gene Silencing in Vivo", *Angew. Chem. Int. Ed.* (2012), 51:8529-8533.

(Continued)

*Primary Examiner* — Patricia L Morris

(74) *Attorney, Agent, or Firm* — Fish & Richardson P.C.

(57) ABSTRACT

The present invention provides a cationic lipid which can be used for nucleic acid delivery to a cytoplasm and which is possible to solve the problem of physical stability of a lipid complex. This cationic lipid is a compound represented by the general formula (3) or a pharmaceutically acceptable salt thereof:

(3)

wherein, L is an alkyl having 7-12 carbon atoms or an alkenyl having 7-12 carbon atoms, R is an alkyl having 1-2 carbon atoms, and $n_1$ and $n_2$ are independently an integer of 1-3.

2 Claims, 1 Drawing Sheet

(56) References Cited

OTHER PUBLICATIONS

Wan et al., "Lipid nanoparticle delivery systems for siRNA-based therapeutics," Drug Delivery and Translational Research, Spring, Germany, 4(1):74-83 (2013).
Written Opinion of the International Searching Authority issued in International Application No. PCT/JP2015/050295, dated Feb. 17, 2015, with English Translation.
Decision to Grant a Patent for corresponding Japanese Patent Application No. 2015-556822 dated Jul. 31, 2018, with English translation.
Communication from the European Patent Office for corresponding EP Patent Application No. 15735252.7 dated Jul. 12, 2018.
The People's Republic of China State Intellectual Property Office, Notice of Allowance dated Jul. 10, 2018 for corresponding CN Patent Application No. 201580003735.2 with English translation.
Office Action issued for Taiwanese Patent Application No. 104100437 dated Aug. 31, 2018, with English translation.

CATIONIC LIPID

Priority is claimed on U.S. Provisional Patent Application Ser. No. 61/925,267, filed in the United States on Jan. 9, 2014, the content of which is incorporated herein by reference.

TECHNICAL FIELD

The present invention relates to novel cationic lipids.

BACKGROUND OF THE INVENTION

Nucleic acids such as siRNA (small interfering RNA), miRNA (micro RNA), shRNA (short hairpin RNA or, small hairpin RNA) expression vector, or, antisense oligonucleotides are nucleic acids which induce inhibition of sequence-specific gene expression in vivo, and are known as nucleic acid medicines.

Among these nucleic acid medicines, in particular, siRNA has attracted attention. siRNA is a double stranded RNA having 19-23 base pairs, and induces inhibition of sequence-specific gene expression called RNA interference (RNAi).

However, although siRNA is chemically-stable, there are problems in therapeutic applications. For example, it is degraded by RNase (ribonuclease) in plasma, and it hardly penetrates the cell membrane alone (e.g., Patent Document 1).

To address the problem, it is known that an encapsulated siRNA is protected from degradation in plasma by encapsulating siRNA into fine particles containing cationic lipids, and it is possible to penetrate lipophilic cell membranes. As lipid particles containing cationic lipids, a lipid formulation containing certain cationic lipids, which are prepared by an extrusion method or an in-line mixing process, has been proposed (e.g., see Patent Document 1.).

The lipid formulation described in Patent Document 1 is a nucleic acid-lipid particle composition which is obtained by encapsulating a polymer such as nucleic acids in fine particles, and Patent Document 1 discloses that it is possible to introduce nucleic acids into cells.

Further, various compounds as cationic lipids which are expected to be used in application of nucleic acid medicines have been developed (e.g., Patent Documents 2-6, and Non-Patent Document 1). However, it is known that there are problems in physical stability in that the particle size of lipid nanoparticles (LNPs) containing cationic lipids with an asymmetrical structure increases during storage (non-Patent Document 2).

For solving the problem, Non-Patent Document 2 discloses that it is possible to suppress an increase of particle size by selectively-using certain phospholipids in LNPs containing cationic lipids having an asymmetric structure.

[Patent Document 1] Japanese Unexamined Patent Publication No. 2012-530,059
[Patent Document 2] International Publication No. 2012/040,184
[Patent Document 3] International Publication No. 2013/059,496
[Patent Document 4] International Publication No. 2010/144,740
[Patent Document 5] US Publication No. 2013/0178541
[Patent Document 6] U.S. Pat. No. 8,158,601
[Non-Patent Document 1] Angew. Chem. Int. Ed. 2012, 51, 8529-8533
[Non-Patent Document 2] Mol. Pharmaceutics 2014, 3, 11 (11), 4143-53

SUMMARY OF THE INVENTION

However, despite recent progress, cationic lipids which are used as nucleic acids delivery to cytoplasm and are possible to solve the problems of physical stability as described above are still necessary.

The cationic lipid of the present invention is a compound represented by the following general formula (1) or a pharmaceutically acceptable salt thereof:

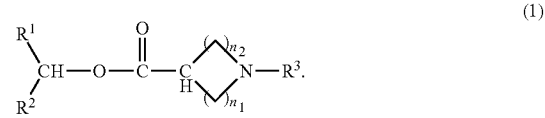

In the above general formula (1), $R^1$ and $R^2$ are independently an alkyl having 4 to 24 carbon atoms or an alkenyl having 4-24 carbon atoms, $n_1$ and $n_2$ are independently an integer of 1-3, and $R^3$ is an alkyl having 1 to 3 carbon atoms.

In the above general formula (1), $R^1$ may have one or more cyclopropane structures formed by condensation of part of the carbon chain.

In the above general formula (1), $R^1$ may have one cyclopropane structure formed by condensation of part of the carbon chain.

The cationic lipid of the present invention wherein in the above general formula (1), $R^1$ is represented by the following formula (2):

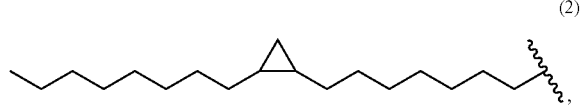

$R^2$ is L which is an alkyl having 7 to 12 carbon atoms or an alkenyl having a carbon number of 7-12, and $R^3$ is R which is an alkyl having 1 or 2 carbon atoms, is represented by the following general formula (3):

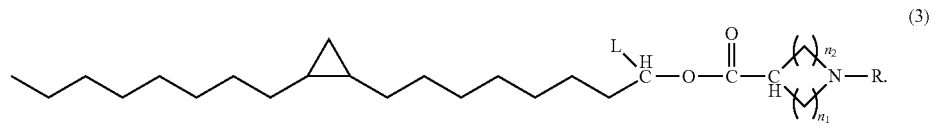

The cationic lipid of the invention may be a compound represented by the general formula (3), wherein $n_1$ and $n_2$ are independently an integer of 1 to 2.
The cationic lipid of the present invention may be a compound selected from the following compounds, or a pharmaceutically acceptable salt thereof:
(4)
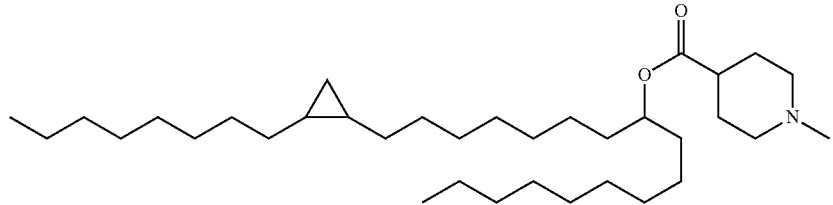
(5)
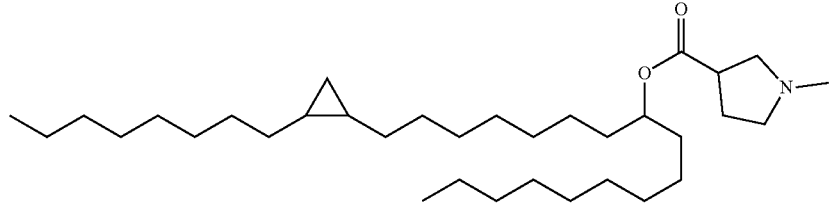
(6)
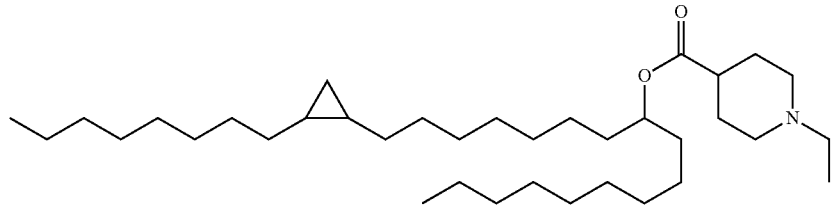
(7)
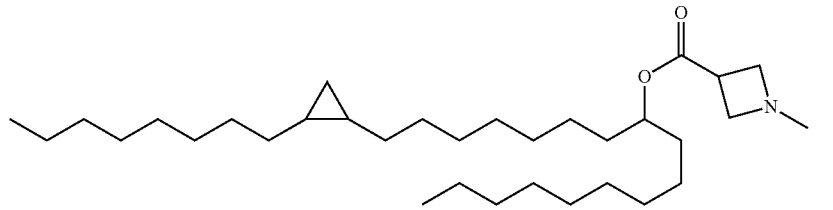
(8)
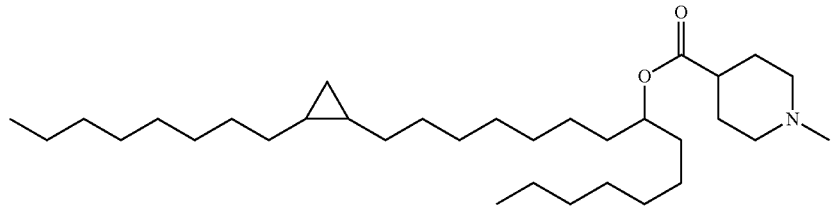
(9)
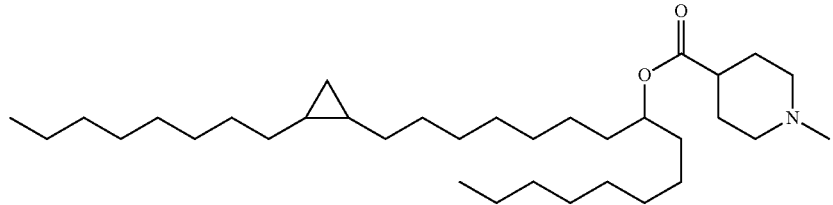
(10)
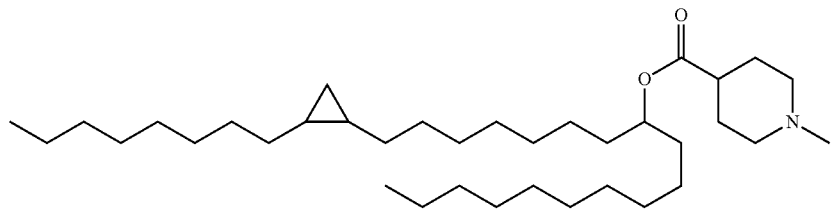

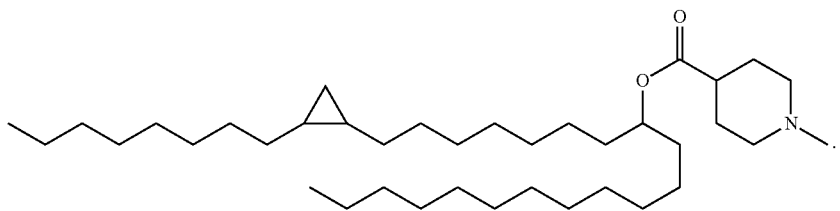

The cationic lipid of the present invention may be a compound represented by the following formula (4), or a pharmaceutically acceptable salt thereof.

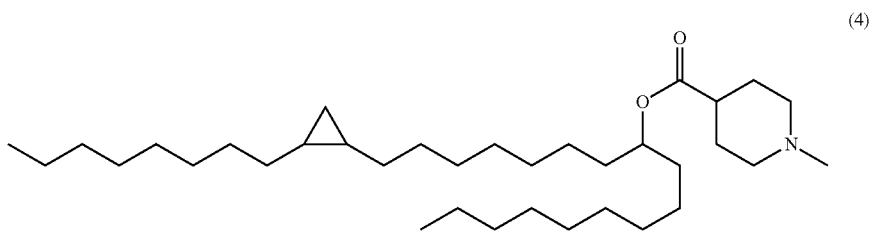 [SMILES: CCCCCCCCCC(CCCCCCCC1CC1CCCCCCCC)OC(=O)C1CCN(C)CC1]

The cationic lipid of the present invention may be a compound represented by the following formula (5), or a pharmaceutically acceptable salt thereof.

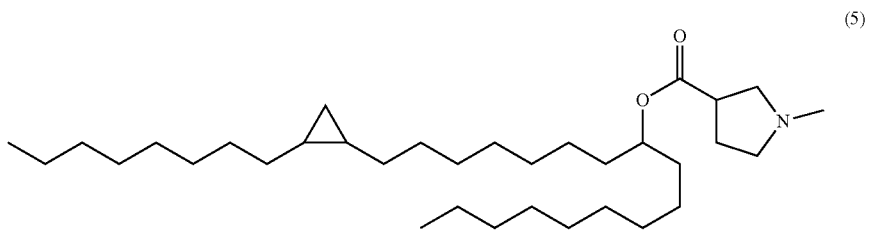 [SMILES: CCCCCCCCCC(CCCCCCCC1CC1CCCCCCCC)OC(=O)C1CCN(C)C1]

The cationic lipids of the present invention may be a compound represented by the following formula (10), or a pharmaceutically acceptable salt thereof.

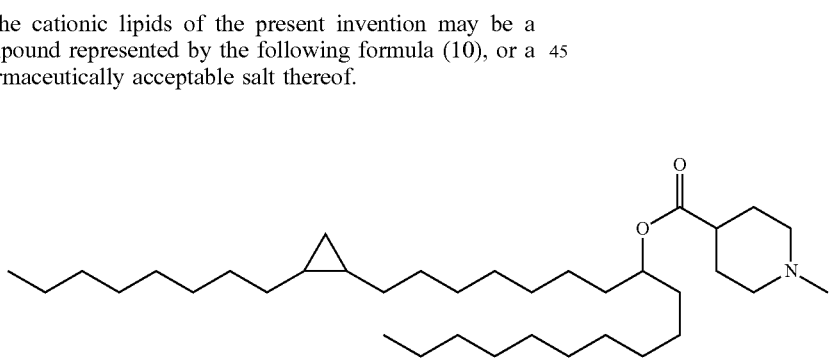

The composition of the present invention contains (I) the cationic lipid of the present invention; (II) at least a lipid selected from the group consisting of neutral lipids, polyethylene glycol-modified lipids and sterol; and (III) a nucleic acid.

The compositions of the present invention is produced by a method including the steps of obtaining a mixed liquid by mixing a polar organic solvent-containing aqueous solution containing (I) the cationic lipid of the present invention and (II) at least a lipid selected from the group consisting of neutral lipids, polyethylene glycol-modified lipids and sterol; and (III) an aqueous solution containing a nucleic acid; and reducing content of the polar organic solvent in the mixed liquid.

It is possible to release efficiently the nucleic acid into the cytoplasm by using the cationic lipid of the present invention. Further, it is possible to solve the problems of physical stability as described above by using the cationic lipid of the present invention. Thus, the cationic lipid of the present invention has applicability as a lipid for nucleic acid delivery into the cytoplasm.

DETAILED DESCRIPTION OF THE INVENTION

«Cationic Lipid»

Figure 1:
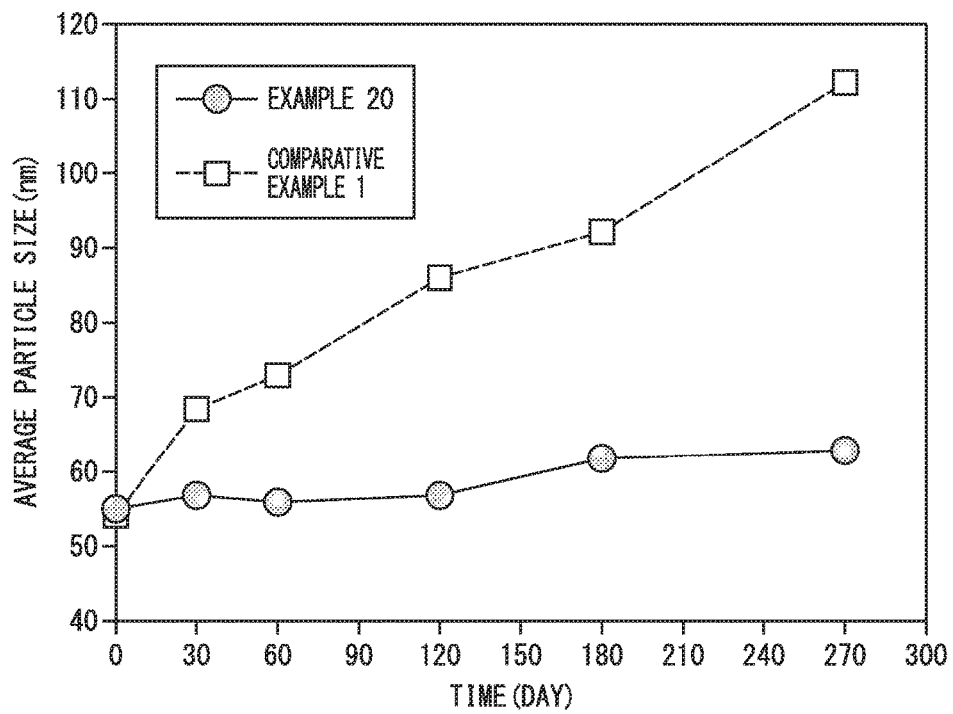
FIG. 1 shows time-dependent variation in average particle size of the compositions of Example 20 and Comparative Example 1.

In one embodiment, the present invention provides a cationic lipid which is a compound represented by the following general formula (1), or a pharmaceutically acceptable salt thereof. The cationic lipid may be a hydrate of the salt or a solvate of the salt.

$$\begin{array}{c}
R^1 \\
\phantom{R^1}\diagdown \\
\phantom{R^1}CH-O-\overset{O}{\underset{\|}{C}}-\underset{H}{C}\underset{(\phantom{x})_{n_1}}{\overset{(\phantom{x})_{n_2}}{\diagup\diagdown}}N-R^3 \\
R^2\diagup
\end{array} \quad (1)$$

In the general formula (1), $R^1$ and $R^2$ are independently an alkyl having 4 to 24 carbon atoms, or an alkenyl having a carbon number of 4-24, $n_1$ and $n_2$ are independently an integer of 1-3, and $R^3$ is an alkyl having 1 to 3 carbon atoms.

In the general formula (1), $R^1$ may have one or more cyclopropane structures formed by condensation of part of the carbon chain, or have one cyclopropane structure.

The cationic lipid of the invention wherein in the above general formula (1), $R^1$ is represented by the formula (2):

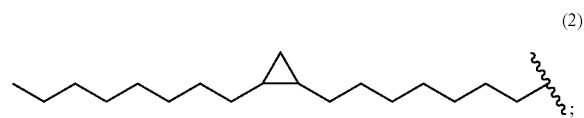

(2)

$R^2$ is L which is an alkyl having 7 to 12 carbon atoms, or, an alkenyl having 7 to 12 carbon atoms; and $R^3$ is R which is an alkyl of 1 or 2 carbon atoms, is a compound represented by the general formula (3):

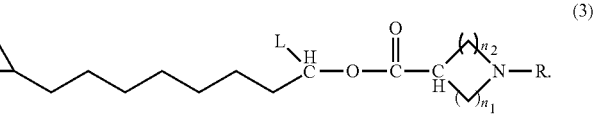

(3)

As the cationic lipid of the invention, in the general formula (3), $n_1$ and $n_2$ may be independently an integer of 1-2.

In the present invention, the cationic lipid is an amphiphilic molecule as represented by the following formula, which includes a lipophilic region X containing one or more hydrocarbon groups and a hydrophilic region Z containing a polar group to be protonated at physiological pH. The cationic lipid of the present invention may further contain a linker region Y between the lipophilic region and the hydrophilic region.

X—Y—Z

As used herein, the term "alkyl" means a saturated aliphatic hydrocarbon group having a specified number of carbon atoms, and the saturated aliphatic hydrocarbon group may have a straight, cyclic or branched chain.

In the present specification, the term "alkenyl" means an unsaturated aliphatic hydrocarbon group having the number of carbon atoms of the specified number, and the unsaturated aliphatic hydrocarbon group may have a straight, cyclic or branched chain. An example of the unsaturated aliphatic hydrocarbon group may be diene, triene, tetraene or like, but is not limited to these.

An Example of cyclic "alkyl" or cyclic "alkenyl" may be a compound having one or more rings formed by fusing part of the carbon chain, such as cyclopropane or cyclobutane, but is not limited to these.

The compound represented by the general formula (3) includes the following compounds:

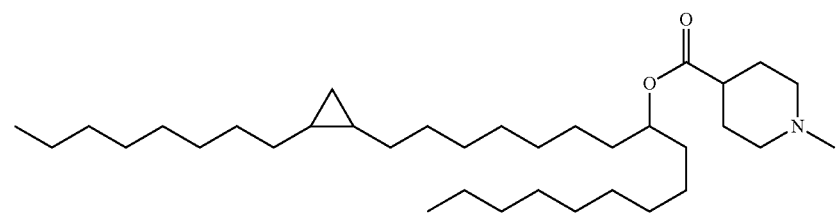

(4)

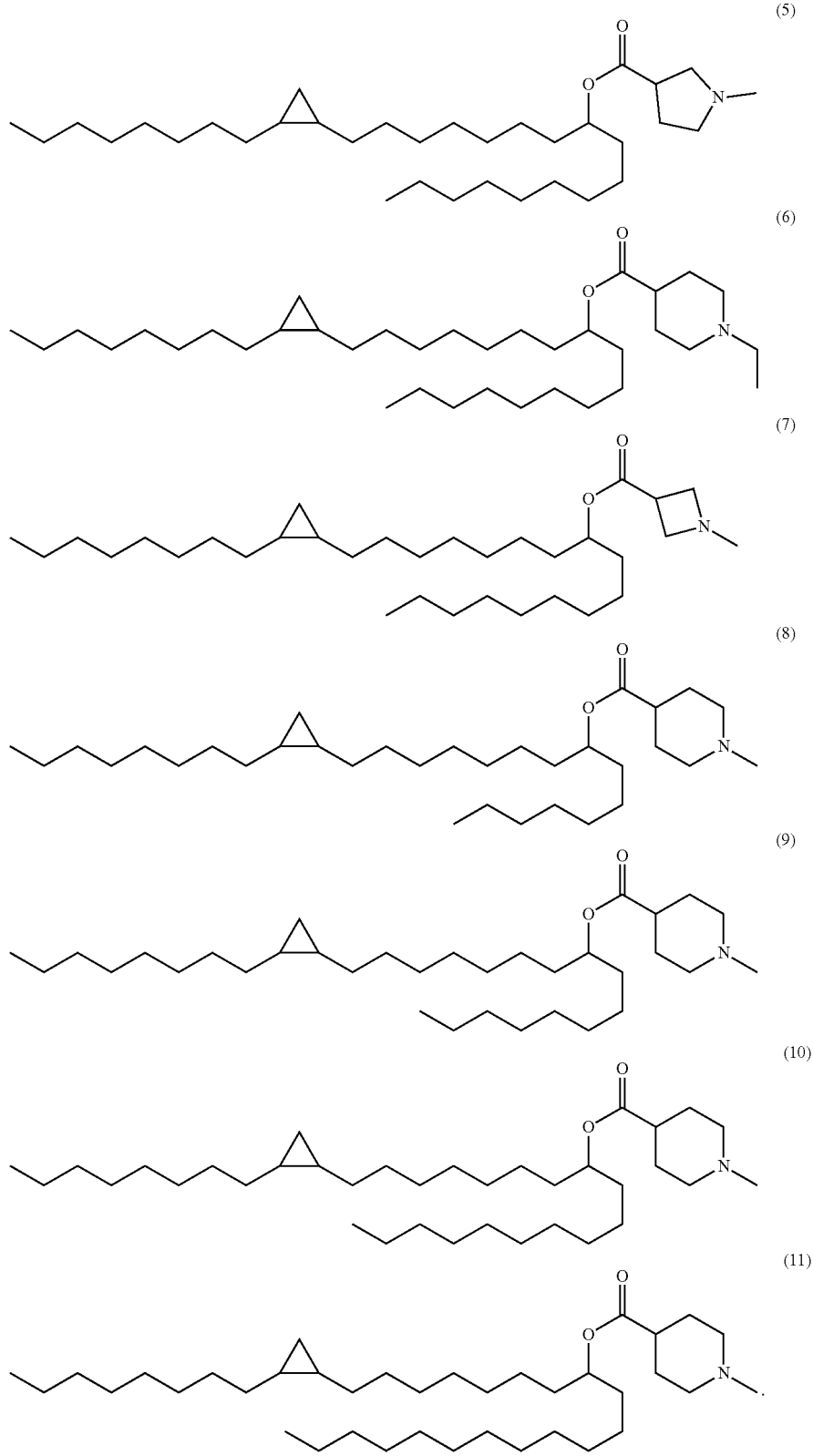
The cationic lipid of the present invention is a compound represented by the general formula (1), or a pharmaceutically acceptable salt. That is, the cationic lipid of the present invention may contain a cation represented by the following general formula (1'), which is obtained by protonating the compound:

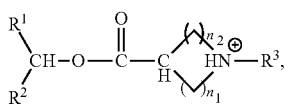

(1')

wherein, in the general formula (1'), $R^1$ to $R^3$, $n_1$ and $n_2$ represent the same meaning as those in the general formula (1).

An anion contained in the cationic lipid of the present invention, which forms an ion pair with the cation represented by the general formula (1') of the present invention, is not particularly limited as long as it is pharmaceutically acceptable. The anion, for example, may be an inorganic ion such as chloride ion, bromide ion, nitrate ion, sulfate ion, or phosphate ion; or an organic acid ion such as acetate ion, oxalate ion, maleate ion, fumarate ion, citrate ion, benzoate ion, methane sulfonate ion.

«Method of Producing Cationic Lipid»

A method of producing a cationic lipid of the present invention is described below. The following formula (12) and formula (13) show an embodiment of synthesis schemes of the cationic lipid.

Synthesis Scheme 1

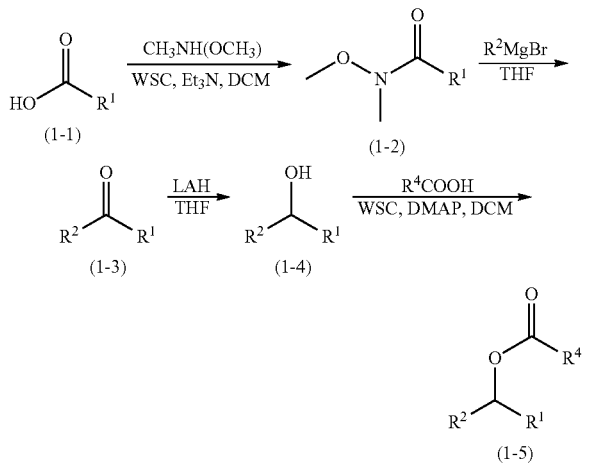

(12)

Synthesis Scheme 2

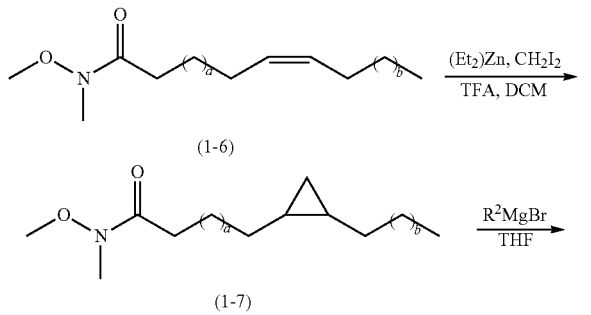

(13)

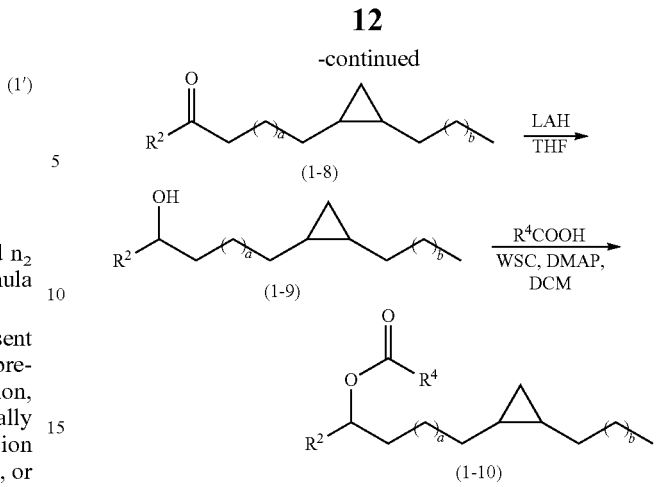

In the formula, $R^4$ is represented by the following general formula (14).

(14)

In the formula, $R^3$, $n_1$ and $n_2$ represent the same meaning as those in the general formula (1), respectively.

In the formula, a and b are an integer of 0 or more, and the sum of a and b is 17 or less.

A novel cationic lipid (1-5) may be synthesized, for example, in accordance with the synthetic scheme 1. A Weinreb amide (1-2) is obtained by condensation of a compound (1-1) and a N,O-dimethyl hydroxylamine. A ketone (1-3) is obtained by adding a Grignard reagent. Further, an alcohol (1-4) is obtained by reduction with a lithium aluminum hydride. An ester (1-5) is obtained by condensation of a carboxylic acid and the alcohol (1-4).

A novel cationic lipid (1-10) including cyclopropyl may be synthesized, for example, in accordance with synthesis scheme 2. A Weinreb amide (1-7) including cyclopropyl is obtained by Simmons-Smith cyclopropanation of an unsaturated Weinreb amide (1-6). A Ketone (1-8) is obtained by adding a Grignard reagent. Further, an alcohol (1-9) is obtained by reduction with a lithium aluminum hydride. An ester (1-10) is obtained by condensation of a carboxylic acid and the alcohol (1-9).

«Composition»

In one embodiment, the present invention provides a composition containing (I) the cationic lipid of the present invention, (II) at least one lipid selected from the group consisting of a neutral lipid, a polyethylene glycol-modified lipid and a sterol, and (III) a nucleic acid.

Hereinafter, preferred embodiments of the composition of the present invention will be described. However, the embodiments are specifically described in order to provide further understanding of the present invention, and are not meant to limit the scope of the present invention, unless otherwise indicated.

The lipid components of the composition of the present embodiment preferably contain 10 mol % to 100 mol % cationic lipids of the present invention, more preferably contain 20 mol % to 90 mol %, and particularly preferably contain 40 mol % to 70 mol %.

The nucleic acid in the composition of the present embodiment includes siRNA, miRNA, shRNA expression vector, antisense oligonucleotide, ribozyme, and the like. siRNA and miRNA are preferred.

The composition of this embodiment preferably contains 0.01 wt % to 50 wt % nucleic acids, and more preferably contains 0.1 wt % to 30 wt % nucleic acids, particularly preferably contains 1 wt % to 10 wt % nucleic acids.

The lipid components in the composition of the present embodiment contain (I) the cationic lipid of present invention, and (II) at least one lipid selected from the group consisting of a neutral lipid, a polyethylene glycol-modified lipid, and a sterol.

The neutral lipid may include dioleoyl-phosphatidylethanolamine (DOPE), palmitoyl-oleoyl-phosphatidylcholine (POPC), egg phosphatidylcholine (EPC), dimyristoyl-phosphatidylcholine (DMPC), dipalmitoyl-phosphatidylcholine (DPPC), distearoyl-phosphatidylcholine (DSPC), diarakidoyl-phosphatidylcholine (DAPC), dibehenoyl-phosphatidylcholine (DBPC), diauroyl-phosphatidylcholine (DLPC), dioleoyl-phosphatidylcholine (DOPC), sphingomyelin, ceramide, dioleoyl-phosphatidyl glycerol (DOPG), dipalmitoyl-phosphatidyl-glycerol (DPPG), phosphatidyl-ethanolamine (POPE), dioleoyl-phosphatidylethanolamine 4-(N-maleimidomethyl)-cyclohexane-1-carboxylate (DOPE-mal), and the like.

The lipid components in the compositions of the present embodiment preferably contain 0 mol % to 50 mol % neutral lipids, more preferably contain 0 mol % to 40 mol % neutral lipids, and particularly preferably contain 0 mol % to 30 mol % neutral lipids.

The polyethylene glycol-modified lipid may include PEG2000-DMG (PEG2000-dimyristylglycerol), PEG2000-DPG (PEG2000-dipalmitoyl glycerol), PEG2000-DSG (PEG2000-distearoylglycerol), PEG5000-DMG (PEG5000-dimyristylglycerol, PEG5000-DPG (PEG5000-dipalmitoyl glycerol), PEG5000-DSG (PEG5000-distearoylglycerol), PEG-cDMA (N-[(methoxy poly (ethylene glycol)2000) carbamyl]-1,2-dimyristyloxypropyl-3-amine), PEG-C-DOMG (R-3-[(ω-methoxy-poly (ethylene glycol) 2000) carbamoyl)]-1,2-dimyristyl-oxyl-3-amine), polyethylene glycol (PEG)-diacylglycerol (DAG), PEG-dialkyloxypropyl (DAA), PEG-phospholipid, PEG-ceramide (Cer), and the like.

The PEG-dialkyloxypropyl includes PEG-dilauryloxypropyl propyl, PEG-dimyristyloxypropyl, PEG-dipalmityl oxypropyl, PEG-distearyl oxy-propyl and the like.

The lipid components in the composition of this embodiment preferably contain 0 mol % to 30 mol % polyethylene glycol-modified lipids, more preferably contain 0 mol % to 20 mol %, particularly preferably contains 0 mol % to 10 mol %.

The sterol may include cholesterol, dihydrocholesterol, lanosterol, β-sitosterol, campesterol, stigmasterol, brassicasterol, ergo Castellammare roll, fucosterol, 3β-[N—(N',N'-dimethyl amino ethyl) carbamoyl]cholesterol (DC-Chol), and the like.

The lipid components in the composition of the present embodiment preferably contain 0 mol % to 90 mol % sterol, more preferably contain 10 mol % to 80 mol %, and particularly preferably contain 20 mol % to 50 mol %.

The combination of the lipid components in the composition of the present embodiment is not particularly limited, for example, may be a combination of the cationic lipid of the present invention, and neutral lipid and sterol; or, preferably a combination of the cationic lipid of the present invention, neutral lipids, polyethylene glycol-modified lipids and the sterol.

The composition of the present embodiment may further contain sugars such as sucrose, glucose, sorbitol, lactose; amino acids such as glutamine, glutamic acid, sodium glutamate, or histidine; and salts of acids such as citric acid, phosphoric acid, acetic acid, lactic acid, carbonic acid or tartaric acid.

The compositions of the present embodiment may also be formulated as a pharmaceutical composition. As the dosage form of the pharmaceutical composition, for example, injection agents may be used.

The compositions of the present embodiment, for example, may be in a powder state obtained by removing the solvent by freeze-drying or the like, or in a liquid state. When the composition is in a powder state, it may be suspended or dissolved by pharmaceutically-acceptable medium prior to use, and the resulting liquid is used as an injection. When the composition is in a liquid state, it may be used as an injection directly or it is suspended or dissolved by a pharmaceutically-acceptable medium, and the resulting liquid is used as an injection.

The pharmaceutically-acceptable medium may include sterile water; saline; and isotonic solution containing adjuvant such as glucose, D-sorbitol, D-mannose, D-mannitol, or sodium chloride. The compositions of the present embodiment may further contain an additive including a solubilizing agent such as alcohol including ethanol, propylene glycol, polyethylene glycol and the like; stabilizer; antioxidant; preservative and the like.

The composition of the present embodiment forms a lipid complex which is formed by encapsulating nucleic acids in microparticles composed of lipids containing cationic lipids. The "average particle size" of the lipid complex may be calculated by any one of a volume-average method, number-average method, and Z-average method. In the composition of the present embodiment, the average particle size (Z-Average) of the lipid complexes is, for example, preferably 10 nm to 1000 nm, more preferably 30 nm to 500 nm, and particularly preferably 30 nm to 200 nm.

It is preferable that during storage, the particle size of the composition of the embodiment increase as little as possible with respect to that before storage. For example, the particle size which is stored for 6 months at 4° C. is preferably 1.6 times or less with respect to that of before storage, more preferably 1.3 times or less, and particularly preferably 1.2 times or less.

It is preferable that there be almost no charge on the surface of the composition of the present embodiment in an environment of about 7.4 pH (e.g., in blood) in order to make it difficult to cause nonspecific adsorption and immune responses. It is preferable that the compositions of this embodiment be positively charged in a low pH environment, in order to make them easy to fuse with endosomal membranes when taken into the cell by endocytosis.

«Production Method of Composition»

In one embodiment of the present invention, a method of producing the composition of the present invention includes the steps of (a) obtaining a mixture by mixing a polar organic solvent-containing aqueous solution containing (I) the cationic lipid of the present invention and (II) at least one lipid selected from the group consisting of neutral lipid, polyethylene glycol-modified lipid and sterol, and (III) an aqueous solution containing nucleic acids; and (b) reducing the content of the polar organic solvent in the mixed solution.

Hereinafter preferred embodiments of the method for producing the composition of the present invention will be described. However, the embodiments are specifically described in order to provide further understanding to the present invention, and are not meant to limit the scope of the present invention, unless otherwise specified.

A lipid complex in which a nucleic acid is encapsulated within a microparticle composed of lipids may be produced by an electrostatic interaction between water-soluble nucleic acids and cationic lipids described above, and by a hydrophobic interaction between the lipids. For example, the lipid complex may be produced by changing the solubility of the lipid components in a polar organic solvent-containing aqueous solution, wherein the lipid components contain (I) the cationic lipid of the present invention and (II) at least one lipid selected from the group consisting of neutral lipid, polyethylene glycol-modified lipid and sterol. The polar organic solvent may include alcohol such as ethanol.

First, in step (a), a mixture is obtained by mixing a polar organic solvent-containing aqueous solution containing (I) the cationic lipid of the present invention and (II) at least one lipid selected from the group consisting of neutral lipid, polyethylene glycol-modified lipid and sterol; and (III) an aqueous solution containing nucleic acids. The concentration of the polar organic solvent in the aqueous solution containing the polar organic solvent is not particularly limited as long as it is possible for the aqueous solution to dissolve the lipid molecules after mixing an aqueous solution of the nucleic acids.

Subsequently, in step (b), the content of the polar organic solvent is reduced by adding water or the like in the above-mentioned mixed solution. Thus, it is possible to form the lipid complex. In order to form the lipid complex efficiently, it is preferable to reduce sharply the content of the polar organic solvent.

According to the method of producing the composition of the present embodiment, it is possible to obtain lipid complexes in which nucleic acids are efficiently encapsulated in fine particles.

The composition may be used as a pharmaceutical composition when the nucleic acid encapsulated in the composition is a nucleic acid medicine.

EXAMPLE

The present invention is described in more detail using Examples, but the present invention is not limited to the Examples. In addition, compound names in the Examples are named by using Marvin Sketch ver. 5.4 (ChemAxion).
<Synthesis of Cationic Lipid>

[Example 1] Synthesis of 1-(2-octylcyclopropyl) heptadecan-8-yl 1-methylpiperidine-4-carboxylate (Hereinafter Referred to as "Cationic Lipid 1")

Cationic Lipid 1 was synthesized according to the synthetic schemes 1 or 2.
Step 1:
WSC (101.8 g, 531.05 mmol), triethylamine (53.74 g, 531.05 mmol), N, O-dimethyl hydroxylamine hydrochloride (51.8 g, 531.05 mmol) were added into a solution obtained by dissolving oleic acid (75.0 g, 265.5 mmol) in methylene chloride (531.0 mL). After stirring until the next day at room temperature, water was added and the organic layer was separated. After 5 times washing the organic layer with water, it was washed once with 1M sodium hydroxide solution, and dried over anhydrous magnesium sulfate. The drying agent was removed by filtration, and then the filtrate was concentrated under reduced pressure. The resulting crude product 1 (88.92 g) was used in the next step without purification.

Step 2:
Diethyl zinc (764.9 mL, 764.9 mmol [1M solution]) was dissolved in methylene chloride (1416.5 mL), and the solution was cooled to 0° C. TFA (87.2 g, 764.9 mmol) and slowly added dropwise in the solution. After cooling again to 0° C. because the temperature increased, diiodomethane (204.9 g, 764.9 mmol) was added, and the mixture was stirred for 30 minutes at 0° C. The crude product 1 (83.0 g, 255.0 mmol) was added in the solution, and then, the mixture was warmed to room temperature and was stirred for 1 hour. After confirming the end of the reaction, the reaction was quenched with ammonium chloride (300 mL). The organic layer obtained by separation was dried over anhydrous magnesium sulfate. The drying agent was removed by filtration, and the filtrate was concentrated under reduced pressure. Compound 2 (73.0 g) was obtained after purification by using a silica gel column chromatography method.

Step 3:
Compound 2 (17.0 g, 50.07 mmol) was dissolved in THF (100 mL), and then 1M nonylmagnesium bromide (100 mL, 100 mmol) was added dropwise at room temperature under a nitrogen atmosphere. After stirring for 1 hour, the reaction was quenched by adding a sufficient amount of aqueous ammonium chloride solution after confirming the end of the reaction. The reaction solution was washed with water, and the organic layer was dried over anhydrous magnesium sulfate. The drying agent was removed by filtration, and the filtrate was concentrated under reduced pressure. Compound 3 (11.7 g) was obtained by purification by using a silica gel column chromatography method.

Step 4:
Lithium aluminum hydride (2.3 g, 61.47 mmol) was added in a solution obtained by dissolving the obtained Compound 3 (25.0 g, 61.5 mmol) in tetrahydrofuran (123 mL), and then it was heated under reflux for one hour. After confirming the end of the reaction, the reaction was quenched slowly by adding water (2.3 mL), 15% aqueous sodium hydroxide solution (2.3 mL), and water (6.9 mL) in this order to the reaction system. The solution was filtered through Celite, and the filtrate was concentrated under reduced pressure. Compound 4 was obtained by purification by using a silica gel column chromatography method.

Step 5:
WSC (0.47 g, 2.45 mmol), dimethylaminopyridine (0.03 g, 0.24 mmol), 1-methyl-piperidine-4-carboxylic acid (0.35 g, 2.45 mmol) were added in a solution obtained by dissolving the resulting compound (0.5 g, 1.22 mmol) in methylene chloride (4.9 mL). After stirring until the next day at room temperature, water was added and the organic layer was separated. The organic layer was washed 5 times with water, washed once with 1N aqueous sodium hydroxide solution, and dried over anhydrous magnesium sulfate. The drying agent was removed by filtration, and the filtrate was concentrated under reduced pressure. Cationic Lipid 1 (0.2 g, 0.37 mmol) represented by the following formula (4) was obtained by purification by using a silica gel column chromatography method.

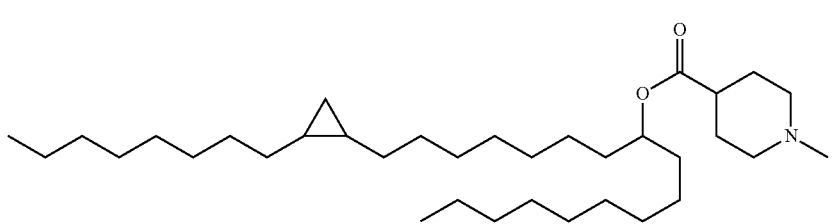
(4)

The obtained compound was confirmed by HPLC-LC/MS under the following conditions. Column: YMC-TriartC18, 150-4.6 mm, 5 μm, eluent: MeOH (uniform solvent), flow rate: 1.0 mL/minute, run-time: 15 minutes, column temperature: 45° C.; detection: UV (215 nm), electro ionization mass spectrometry (ESI-MS).

HPLC-LC/MS, Rt 11.3 min, ESI-MS (M+H) calcd 533.5, found 534.6, $^1$H NMR (400 MHz, CDCl$_3$) 54.87 (1H, q), 2.81 (2H, d), 2.26 (3H, s), 2.23 (1H, yd), 1.98 (2H, t), 1.93 (2H, d), 1.80 (2H, m), 1.50 (4H, m), 1.37 (6H, m), 1.27 (32H, m), 1.13 (2H, s), 0.87 (6H, dd), 0.64 (2H, dd), 0.55 (1H, m), −0.34 (1H, dd)

Examples 2 to 9, Reference Examples 1 to 4

By the same method as in Example 1, the following Cationic Lipids 2 to 13 were synthesized.

[Example 2] 1-(2-octylcyclopropyl)heptadecan-8-yl 1-methylpyrrolidine-3-carboxylate (Cationic Lipid 2)

(5)

HPLC-LC/MS, Rt 11.0 min, ESI-MS (M+H) calcd 519.5, found 520.6, 1H NMR (400 MHz, CDCl3) δ 4.85 (1H, ddd), 3.03 (1H, t), 2.87 (1H, t), 2.64 (1H, dd), 2.59 (1H, dd), 2.47 (1H, d), 2.35 (3H, s), 2.09 (2 h, ddd), 1.50 (4H, m), 1.36-1.25 (37H, m), 1.12 (3H, m), 0.87 (6H, m), 0.62 (2H, dd), 0.55 (1H, m), −0.34 (1H, dd)

[Example 3] 1-(2-octylcyclopropyl)heptadecan-8-yl 1-ethylpiperidine-4-carboxylate (Cationic Lipid 3)

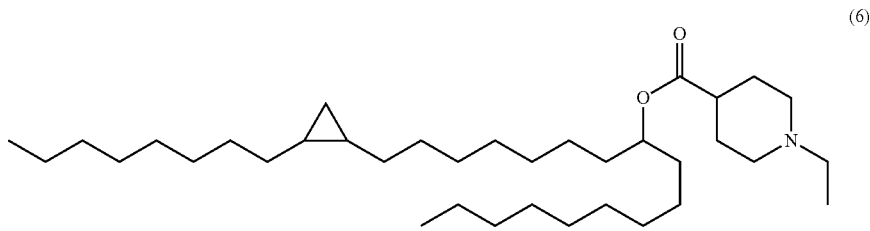 [SMILES: CCCCCCCCCC(CCCCCCCC1CC1CCCCCCCC)OC(=O)C1CCN(CC)CC1]
(6)

HPLC-LC/MS, Rt 12.1 min, ESI-MS (M+H) calcd 547.5, found 548.6, 1H NMR (400 MHz, CDCl3) δ4.88 (1H, ddd), 2.90 (2H, d), 2.49 (2H, dd), 2.27 (1H, m), 1.98 (4H, m), 1.78 (2H, m), 1.49 (4H, m), 1.36-1.25 (37H, m), 1.12 (6H, m), 0.87 (6H, m), 0.62 (2H, dd), 0.55 (1H, m), −0.34 (1H, dd)

[Example 4] 1-(2-octylcyclopropyl)heptadecan-8-yl 1-methylazetidine-3-carboxylate (Cationic Lipid 4)

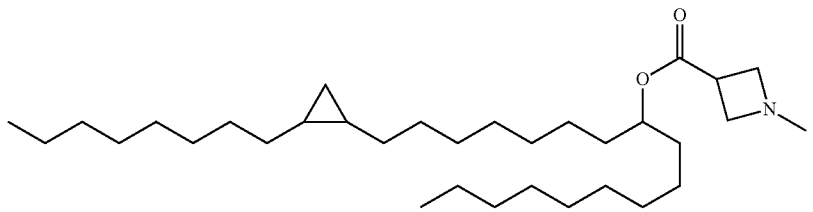

(7)

HPLC-LC/MS, Rt 9.65 min, ESI-MS (M+H) calcd 505.5, found 506.5, 1H NMR (400 MHz, CDCl3) δ4.88 (1H, d), 3.56 (2H, m), 3.26 (3H, m), 2.31 (3H, s), 1.76 (1H, m), 1.51 (4H, m), 1.36-1.25 (36H, m), 1.12 (3H, m), 0.87 (6H, m), 0.62 (2H, dd), 0.55 (1H, m), −0.34 (1H, dd)

[Example 5] 1-(2-octylcyclopropyl)pentadecan-8-yl 1-methylpiperidine-4-carboxylate (Cationic Lipid 5)

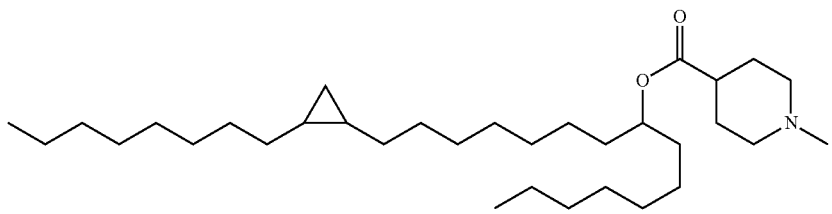

(8)

HPLC-LC/MS, Rt 11.5 min, ESI-MS (M+H) calcd 505.5, found 506.7, 1H NMR (400 MHz, CDCl3) δ4.87 (1H, d), 2.81 (2H, d), 2.33 (3H, s), 2.25 (1H, m), 2.01 (2H, ddd), 1.90 (2H, dd), 1.79 (2H, ddd), 1.72 (1H, m), 1.50 (4H, m), 1.36-1.25 (32H, m), 1.12 (3H, m), 0.87 (6H, m), 0.62 (2H, dd), 0.55 (1H, m), −0.34 (1H, dd)

[Example 6] 1-(2-octylcyclopropyl)hexadecan-8-yl 1-methylpiperidine-4-carboxylate (Cationic Lipid 6)

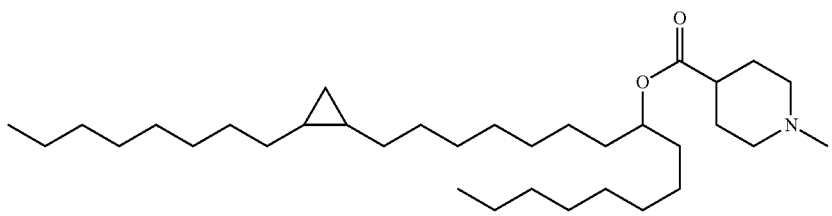

(9)

HPLC-LC/MS, Rt 13.1 min, ESI-MS (M+H) calcd 519.5, found 520.6, 1H NMR (400 MHz, CDCl3) δ4.87 (1H, d), 2.81 (2H, d), 2.33 (3H, s), 2.25 (1H, m), 2.01 (2H, ddd), 1.90 (2H, dd), 1.79 (2H, ddd), 1.72 (1H, m), 1.50 (4H, m), 1.36-1.25 (34H, m), 1.12 (3H, m), 0.87 (6H, m), 0.62 (2H, dd), 0.55 (1H, m), −0.34 (1H, dd)

[Example 7] 1-(2-octylcyclopropyl)octadecan-8-yl 1-methylpiperidine-4-carboxylate (Cationic Lipid 7)

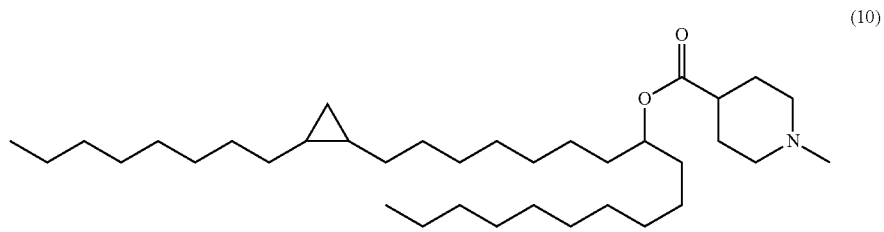 [SMILES: CCCCCCCCCCC(CCCCCCCC1CC1CCCCCCCC)OC(=O)C1CCN(C)CC1]

HPLC-LC/MS, Rt 17.1 min, ESI-MS (M+H) calcd 547.5, found 548.5, 1H NMR (400 MHz, CDCl3) δ4.87 (1H, d), 2.81 (2H, d), 2.33 (3H, s), 2.25 (1H, m), 2.01 (2H, ddd), 1.90 (2H, dd), 1.79 (2H, ddd), 1.72 (1H, m), 1.50 (4H, m), 1.36-1.25 (38H, m), 1.12 (3H, m), 0.87 (6H, m), 0.62 (2H, dd), 0.55 (1H, m), −0.34 (1H, dd)

[Example 8] 1-(2-octylcyclopropyl)icosan-8-yl 1-methylpiperidine-4-carboxylate (Cationic Lipid 8)

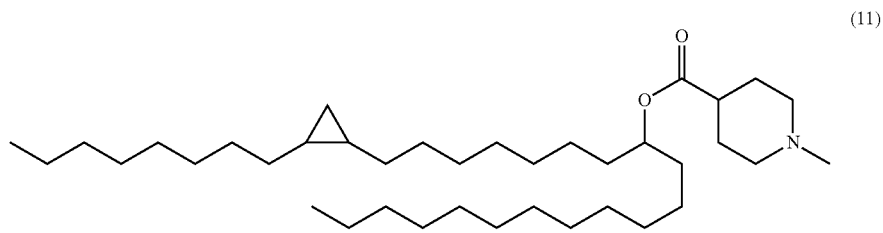 [SMILES: CCCCCCCCCCCCC(CCCCCCCC1CC1CCCCCCCC)OC(=O)C1CCN(C)CC1]

HPLC-LC/MS, Rt 22.6 min, ESI-MS (M+H) calcd 575.5, found 576.5, 1H NMR (400 MHz, CDCl3) δ4.87 (1H, d), 2.81 (2H, d), 2.33 (3H, s), 2.25 (1H, m), 2.01 (2H, ddd), 1.90 (2H, dd), 1.79 (2H, ddd), 1.72 (1H, m), 1.50 (4H, m), 1.36-1.25 (42H, m), 1.12 (3H, m), 0.87 (6H, m), 0.62 (2H, dd), 0.55 (1H, m), −0.34 (1H, dd)

[Example 9] 1-(2-octylcyclopropyl)heptadecan-8-yl 1-ethylpyrrolidine-3-carboxylate (Cationic Lipid 9)

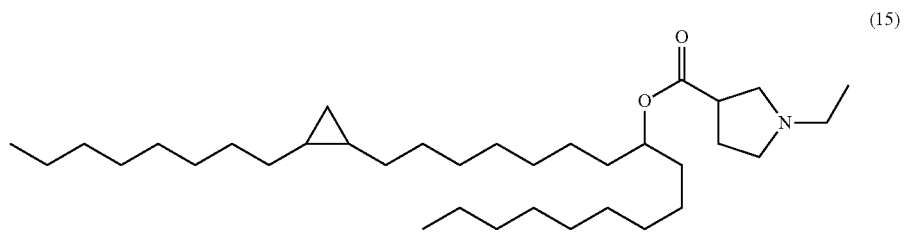 [SMILES: CCCCCCCCCC(CCCCCCCC1CC1CCCCCCCC)OC(=O)C1CCN(CC)C1]

HPLC-LC/MS, Rt 11.9 min, ESI-MS (M+H) calcd 533.5, found 534.6, 1H NMR (400 MHz, CDCl3) δ4.86 (1H, ddd), 3.00 (2H, m), 2.73 (1H, dd), 2.54 (2H, dd), 2.47 (2H, ddd), 2.08 (2H, m), 1.50 (5H, m), 1.36-1.25 (36H, m), 1.12 (6H, m), 0.87 (6H, m), 0.62 (2H, dd), 0.55 (1H, m), −0.34 (1H, dd)

[Reference Example 1] 1-(2-octylcyclopropyl)heptadecan-8-yl 3-(dimethylamino)propanoate (Cationic Lipid 10)

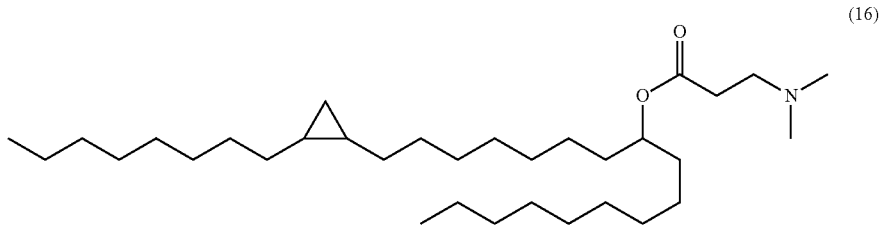 [SMILES: CCCCCCCCCC(CCCCCCCC1CC1CCCCCCCC)OC(=O)CCN(C)C]

(16)

HPLC-LC/MS, Rt 10.4 min, ESI-MS (M+H) calcd 507.5, found 508.6, 1H NMR (400 MHz, CDCl3) δ4.88 (1H, q), 2.61 (2H, dd), 2.45 (2H, dd), 2.24 (6H, s), 1.51 (4H, m), 1.34 (6H, m), 1.27 (32H, m), 1.13 (2H, m), 0.88 (6H, m), 0.64 (2H, m), 0.56 (1H, dd), −0.34 (1H, dd)

[Reference Example 2] 1-(2-octylcyclopropyl)heptadecan-8-yl 4-(dimethylamino)butanoate (Cationic Lipid 11)

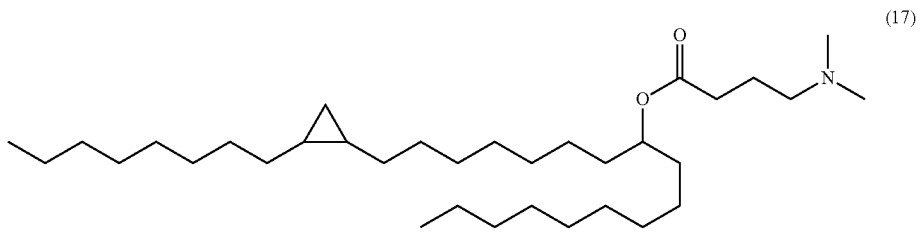 [SMILES: CCCCCCCCCC(CCCCCCCC1CC1CCCCCCCC)OC(=O)CCCN(C)C]

(17)

HPLC-LC/MS, Rt 10.5 min, ESI-MS (M+H) calcd 521.5, found 522.6, 1H NMR (400 MHz, CDCl3) δ4.87 (1H, q), 2.31 (4H, m), 2.21 (6H, s), 2.17 (1H, s), 1.80 (2H, m), 1.61 (1H, s), 1.50 (2H, d), 1.37 (6H, m), 1.27 (32H, m), 1.14 (2H, m), 0.87 (6H, dd), 0.64 (2H, dd), 0.55 (1H, m), −0.34 (1H, dd)

[Reference Example 3] 1-(2-octylcyclopropyl)heptadecan-8-yl 3-(dimethylamino)-2-methylpropanoate (Cationic Lipid 12)

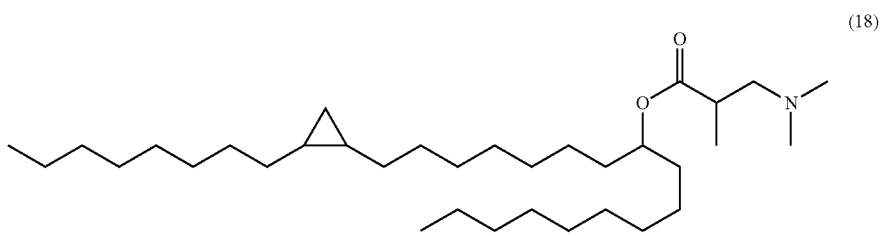 [SMILES: CCCCCCCCCC(CCCCCCCC1CC1CCCCCCCC)OC(=O)C(C)CN(C)C]

(18)

HPLC-LC/MS, Rt 12.5 min, ESI-MS (M+H) calcd 521.5, found 522.6, 1H NMR (400 MHz, CDCl3) δ4.87 (1H, q), 2.66 (2H, t), 2.22 (6H, s), 1.51 (4H, m), 1.36-1.27 (38H, m), 1.15 (6H, m), 0.88 (6H, dd), 0.64 (2H, dd), 0.55 (1H, m), −0.34 (1H, dd)

[Reference Example 4] 1-(2-octylcyclopropyl)heptadecan-8-yl 3-(piperidin-1-yl)propanoate (Cationic Lipid 13)

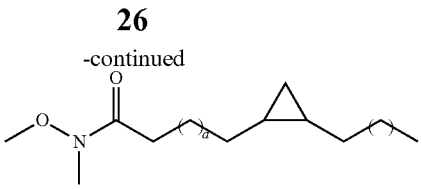

Step 1:
WSC (101.8 g, 531.05 mmol), triethylamine (53.74 g, 531.05 mmol), N,O-dimethyl hydroxylamine hydrochloride

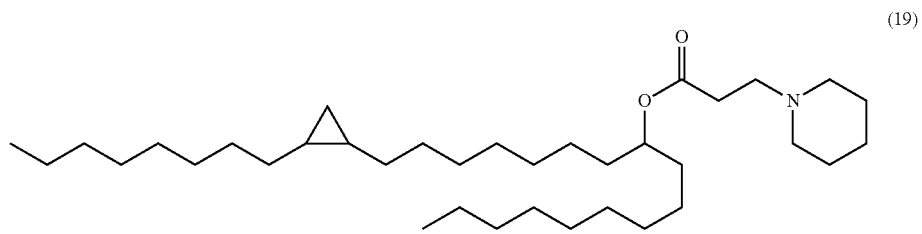 [SMILES: CCCCCCCCCC(CCCCCCCC1CC1CCCCCCCC)OC(=O)CCN1CCCCC1]

(19)

HPLC-LC/MS, Rt 14.1 min, ESI-MS (M+H) calcd 547.5, found 548.6, 1H NMR (400 MHz, CDCl3) δ4.87 (1H, q), 3.59 (2H, m), 2.66 (2H, t), 2.48 (2H, t), 2.39 (2H, m), 1.58 (4H, m), 1.49 (4H, m), 1.43-1.27 (38H, m), 1.13 (4H, m), 0.88 (6H, dd), 0.64 (2H, dd), 0.55 (1H, m), −0.34 (1H, dd)

[Reference Example 5] Synthesis of 2-(dimethylamino)-N-[1-(2-octylcyclopropyl)heptadecan-8-Yl] acetamide (Hereinafter Referred to as "Cationic Lipid 14")

Cationic Lipid 14 was synthesized in accordance with the following Synthesis Schemes 3 or 4.

Synthesis Scheme 3

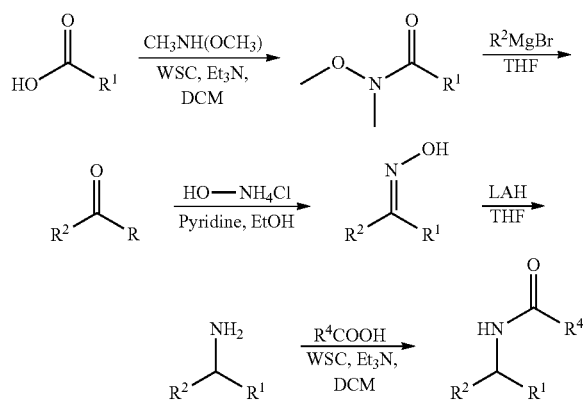

Synthesis Scheme 4

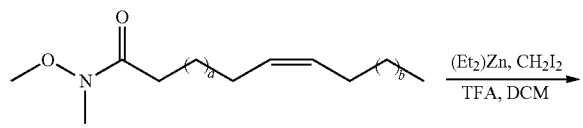

(51.8 g, 531.05 mmol) were added into a solution obtained by dissolving oleic acid (75.0 g, 265.5 mmol) in methylene chloride (531.0 mL). After stirring until the next day at room temperature, water was added and the organic layer was separated. After 5 times washing the organic layer with water, it was washed once with 1 M sodium hydroxide solution, and dried over anhydrous magnesium sulfate. The drying agent was removed by filtration, and then the filtrate was concentrated under reduced pressure. The resulting crude product 1 (88.92 g) was used in the next step without purification.

Step 2:
Diethyl zinc (764.9 mL, 764.9 mmol [1 M solution]) was dissolved in methylene chloride (1416.5 mL), and the solution was cooled to 0° C. TFA (87.2 g, 764.9 mmol) was slowly added dropwise in the solution. After cooling again to 0° C. because the temperature increased, diiodomethane (204.9 g, 764.9 mmol) was added, and the mixture was stirred for 30 minutes at 0° C. The crude product 1 (83.0 g, 255.0 mmol) was added in the solution, and then, the mixture was warmed to room temperature and was stirred for 1 hour. After confirming the end of the reaction, the reaction was quenched with ammonium chloride (300 mL). The organic layer obtained by separation was dried over anhydrous magnesium sulfate. The drying agent was removed by filtration, and the filtrate was concentrated under reduced pressure. Compound 2 (73.0 g) was obtained after purification by using silica gel column chromatography method.

Step 3:
Compound 2 (17.0 g, 50.07 mmol) was dissolved in THF (100 mL), and then 1 M nonylmagnesium bromide (100 mL, 100 mmol) was added dropwise at room temperature under a nitrogen atmosphere. After stirring it for 1 hour, the reaction was quenched by adding a sufficient amount of aqueous ammonium chloride solution after confirming the end of the reaction. The reaction solution was washed with water, and the organic layer was dried over anhydrous magnesium sulfate. The drying agent was removed by filtration, and the filtrate was concentrated under reduced pressure. Compound 3 (11.7 g) was obtained by purification by using a silica gel column chromatography method.

Step 4:

Hydroxylamine hydrochloride (2.4 g, 35.1 mmol) and pyridine (18.0 mL) were added in a solution obtained by dissolving obtained Compound 3 (11.0 g, 27.0 mmol) in ethanol (108 mL). It was stirred at room temperature overnight. The reaction solution was concentrated, extracted with ethyl acetate, and washed with water. The organic layer was dried over anhydrous magnesium sulfate. It was purified by silica gel column chromatography to give Compound 4 (10.8 g).

Step 5:

A solution was obtained by dissolving the obtained Compound 4 (10.0 g, 23.7 mmol) in tetrahydrofuran (237 mL) and was cooled to 0° C. Lithium aluminum hydride (0.9 g, 23.7 mmol) was added in the solution, and then it was heated under reflux for one hour. After confirming the end of the reaction, the reaction was quenched slowly by adding water (0.9 mL), 15% aqueous sodium hydroxide solution (0.9 mL), and water (2.7 mL) in this order to the reaction system. The solution was filtered through Celite, and the filtrate was concentrated under reduced pressure. Compound 5 (5.5 g) was obtained by purification by using a silica gel column chromatography method.

Step 6:

WSC (0.47 g, 2.45 mmol), triethylamine (0.25 g, 2.45 mmol), N, N-dimethyl glycine (0.25 g, 2.45 mmol) were added in a solution obtained by dissolving the resulting compound (0.5 g, 1.23 mmol) in methylene chloride (4.9 mL). After stirring until the next day at room temperature, water was added and the organic layer was separated. The organic layer was washed 5 times with water, washed once with 1 N aqueous sodium hydroxide solution, and dried over anhydrous magnesium sulfate. The drying agent was removed by filtration, and the filtrate was concentrated under reduced pressure. Cationic Lipid 14 (0.4 g, 0.8 mmol) represented by the following formula (20) was obtained by purification by using a silica gel column chromatography method.

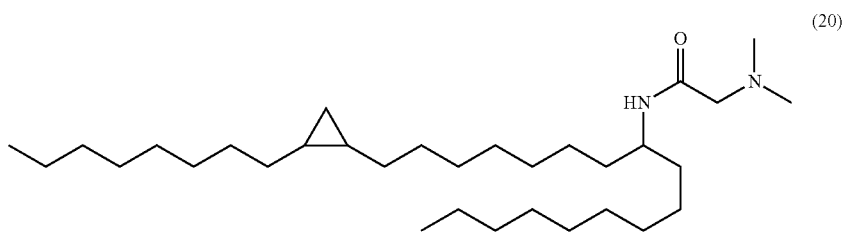 [SMILES: CCCCCCCCCC(CCCCCCCC1CC1CCCCCCCC)NC(=O)CN(C)C]

(20)

HPLC-LC/MS, Rt 6.91 min, ESI-MS (M+H) calcd 492.5, found 493.6, $^1$H NMR (400 MHz, CDCl$_3$) δ6.84 (1H, d), 3.88 (1H, dd), 2.93 (2H, s), 2.29 (6H, s), 1.64 (1H, m), 1.49 (2H, m), 1.27 (39H, m), 0.89 (2H, m), 0.88 (6H, m), 0.64 (2H, m), 0.56 (1H, dd), −0.34 (1H, dd)

Reference Example 6 to 13

In the same manner as described in Reference Example 5, the following Cationic Lipids 15-22 were synthesized according to the synthetic schemes 3 or 4.

[Reference Example 6] 3-(dimethylamino)-N-[1-(2-octylcyclopropyl)heptadecan-8-yl]propanamide (Cationic Lipid 15)

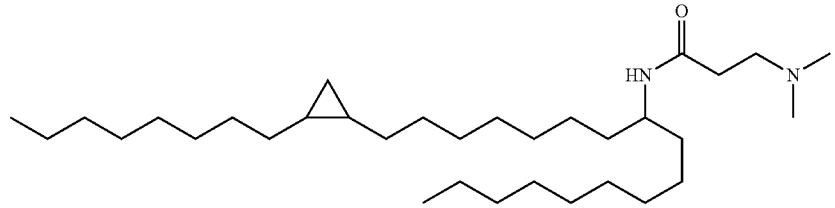

(21)

HPLC-LC/MS, Rt 7.10 min, ESI-MS (M+H) calcd 506.5, found 507.5, 1H NMR (400 MHz, CDCl3) δ6.84 (1H, d), 3.88 (1H, dd), 2.93 (2H, s), 2.29 (6H, s), 1.64 (1H, m), 1.49 (2H, m), 1.27 (41H, m), 0.89 (2H, m), 0.88 (6H, m), 0.64 (2H, m), 0.56 (1H, dd), −0.34 (1H, dd)

[Reference Example 7] 4-(dimethylamino)-N-[1-(2-octylcyclopropyl)heptadecan-8-yl] butanamide (Cationic Lipid 16)

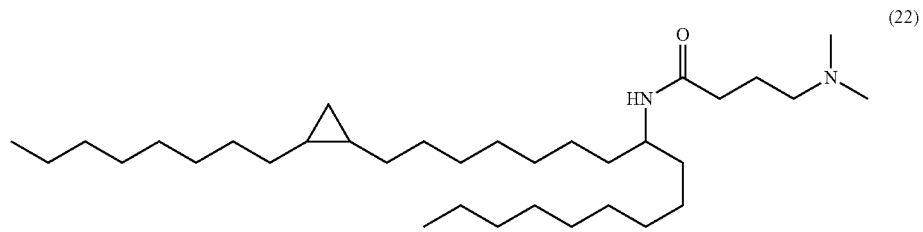 [SMILES: CCCCCCCCCC(CCCCCCCC1CC1CCCCCCCC)NC(=O)CCCN(C)C]

(22)

HPLC-LC/MS, Rt 7.20 min, ESI-MS (M+H) calcd 520.5, found 521.5, 1H NMR (400 MHz, CDCl3) δ6.06 (1H, d), 3.88 (1H, dd), 2.28 (4H, m), 2.21 (6H, s), 1.78 (2H, q), 1.64 (4H, s), 1.27 (40H, m), 0.88 (6H, m), 0.64 (2H, m), 0.56 (1H, dd), −0.34 (1H, dd)

[Reference Example 8] 2-(dimethylamino)-N-[(20Z,23Z)-heptacosa-20,23-dien-10-yl] acetamide (Cationic Lipid 17)

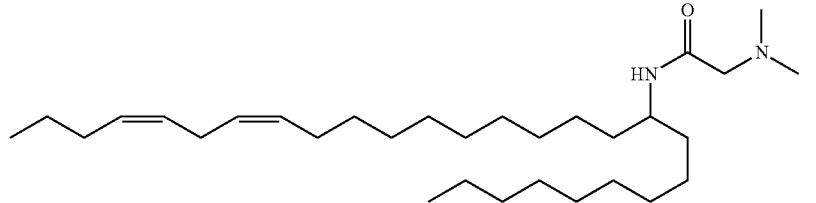

(23)

HPLC-LC/MS, Rt 6.50 min, ESI-MS (M+H) calcd 476.5, found 477.5, 1H NMR (400 MHz, CDCl3) δ6.84 (1H, d), 5.35 (4H, m), 3.88 (1H, dd), 2.93 (2H, s), 2.77 (2H, t), 2.29 (6H, s), 2.17 (2H, s), 2.05 (4H, m), 1.63 (4H, m), 1.36 (3H, t), 1.25 (25H, m), 0.88 (6H, dd)

[Reference Example 9] 2-(dimethylamino)-N-[(18Z)-heptacos-18-en-10-yl] acetamide (Cationic Lipid 18)

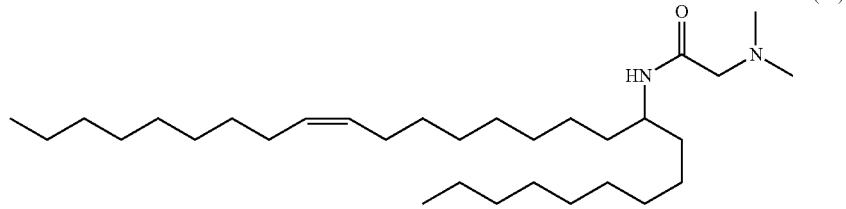

(24)

HPLC-LC/MS, Rt 7.98 min, ESI-MS (M+H) calcd 478.5, found 479.5, 1H NMR (400 MHz, CDCl3) δ6.83 (1H, d), 5.36 (2H, m), 3.88 (2H, m), 3.74 (1H, t), 2.93 (2H, s), 2.28 (2H, m), 2.17 (2H, s), 2.00 (3H, m), 1.85 (1H, m), 1.50 (3H, m), 1.25 (37H, m), 0.86 (6H, dd)

[Reference Example 10] 1-methyl-N-[1-(2-octylcyclopropyl) heptadecan-8-yl] pyrrolidine-2-carboxamide (Cationic Lipid 19)

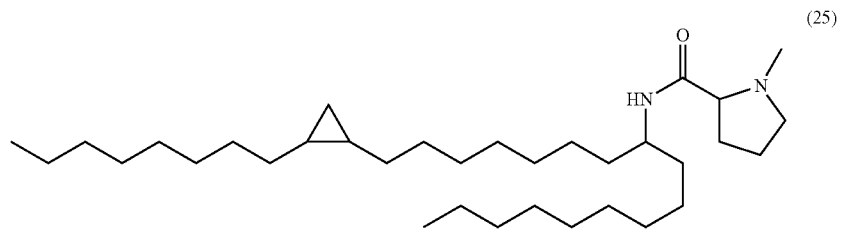 [SMILES: CCCCCCCCCC(CCCCCCCC1CC1CCCCCCCC)NC(=O)C1CCCN1C]
(25)

HPLC-LC/MS, Rt 8.14 min, ESI-MS (M+H) calcd 518.5, found 519.7, 1H NMR (400 MHz, CDCl3) δ6.99 (1H, d), 3.85 (1H, m), 3.07 (1H, m), 2.85 (1H, m), 2.35 (3H, s), 2.33 (2H, m), 2.23 (1H, m), 1.76 (4H, m), 1.47 (4H, m), 1.26-1.25 (35H, m), 1.12 (3H, m), 0.87 (6H, m), 0.62 (2H, dd), 0.55 (1H, m), −0.34 (1H, dd)

[Reference Example 11] 1-ethyl-N-[1-(2-octylcyclopropyl)heptadecan-8-yl] pyrrolidine-2-carboxamide (Cationic Lipid 20)

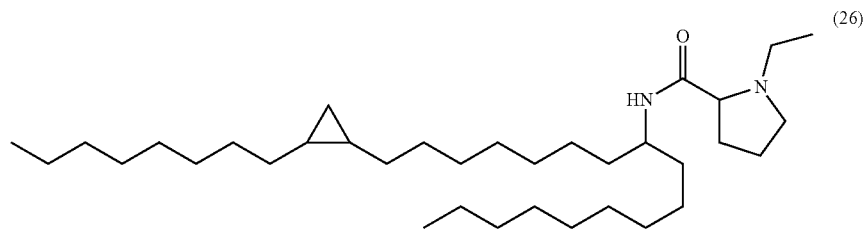 [SMILES: CCCCCCCCCC(CCCCCCCC1CC1CCCCCCCC)NC(=O)C1CCCN1CC]
(26)

HPLC-LC/MS, Rt 8.95 min, ESI-MS (M+H) calcd 532.5, found 533.6, 1H NMR (400 MHz, CDCl3) δ7.17 (1H, d), 3.84 (1H, m), 3.16 (1H, t), 3.00 (1H, dd), 2.64 (1H, ddd), 2.47 (1H, ddd), 2.27 (1H, ddd), 2.15 (1H, ddd), 1.76 (4H, m), 1.47 (2H, m), 1.26-1.25 (37H, m), 1.12 (3H, m), 1.06 (4H, m), 0.87 (6H, m), 0.62 (2H, dd), 0.55 (1H, m), −0.34 (1H, dd)

[Reference Example 12] 1-methyl-N-[1-(2-octylcyclopropyl)heptadecan-8-yl] piperidine-2-carboxamide (Cationic Lipid 21)

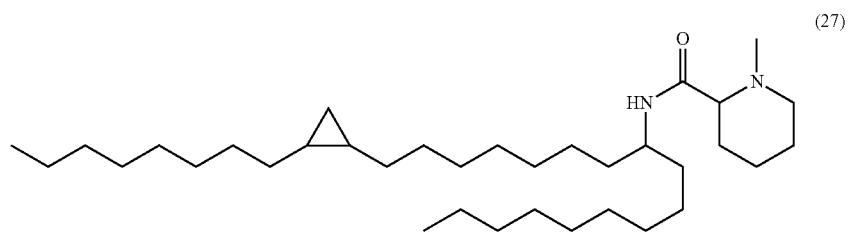 [SMILES: CCCCCCCCCC(CCCCCCCC1CC1CCCCCCCC)NC(=O)C1CCCCN1C]
(27)

HPLC-LC/MS, Rt 7.43 min, ESI-MS (M+H) calcd 532.5, found 533.6, 1H NMR (400 MHz, CDCl3) δ 6.28 (1H, d), 3.88 (1H, m), 2.89 (1H, d), 2.42 (1H, dd), 2.21 (3H, s), 2.00 (2H, m), 1.72 (2H, m), 1.49 (4H, m), 1.26-1.25 (40H, m), 1.12 (3H, m), 0.87 (6H, m), 0.62 (2H, dd), 0.55 (1H, m), −0.34 (1H, dd)

[Reference Example 13] 1-ethyl-N-[1-(2-octylcyclopropyl) heptadecan-8-yl]piperidine-2-carboxamide (Cationic Lipid 22)

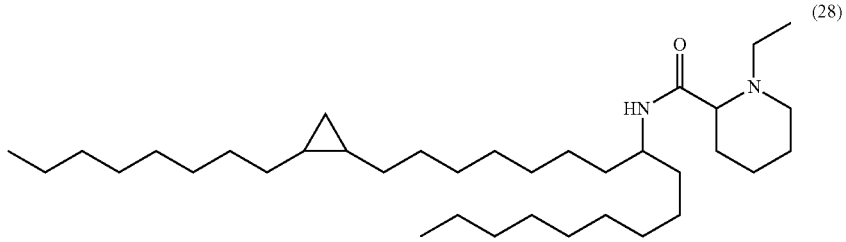 [SMILES: CCCCCCCCCC(CCCCCCCC1CC1CCCCCCCC)NC(=O)C1CCCCN1CC]

(28)

HPLC-LC/MS, Rt 8.03 min, ESI-MS (M+H) calcd 546.6, found 547.6, 1H NMR (400 MHz, CDCl3) δ 3.88 (1H, m), 2.89 (1H, m), 2.85 (1H, m), 2.48 (3H, s), 1.89 (1H, m), 1.76 (2H, m), 1.63 (2H, m), 1.47 (2H, m), 1.26-1.25 (41H, m), 1.12 (6H, m), 0.87 (6H, m), 0.62 (2H, dd), 0.55 (1H, m), −0.34 (1H, dd)

Preparation of Composition (1)

Example 10

The composition was prepared by using Cationic Lipid 1 of Example 1. As the nucleic acid, annealed siRNA (Gene Design Co., hereinafter sometimes referred to as "Factor VII siRNAs") inhibiting expression of factor VII (blood coagulation factor VII) gene which consists of the nucleotide sequence of the sense strand 5'-GGAfUfCAfUfCfUfCAAGfUfCfUfUAfCT*T-3'(SEQ ID NO: 1, T: DNA, fU, fC=2'-Fluoro RNA, *=Phosphorothioate linkage), and the antisense strand 5'-GfUAAGAfCfUfUGAGAfUGAfUfCfCT*T-3'(SEQ ID NO: 2, T: DNA, fU, fC=2'-Fluoro RNA, *=Phosphorothioate linkage) was used.

Factor VII siRNA was dissolved in 25 mM sodium acetate (pH 4.0) to produce 216 μg/mL siRNA diluted solution. In addition, Cationic Lipid 1, DSPC (Nippon Seika Co., Ltd.), Cholesterol (Nippon Seika Co., Ltd.), MPEG2000-DMG (NOF CORPORATION) were dissolved in ethanol in proportion of 60/8.5/30/1.5 (molar ratio) so that the total lipid concentration was 15 mM, to produce a lipid solution. The siRNA diluted solution and the lipid solution were mixed at a flow rate of 2.4 mL/min and 1.29 mL/min, respectively, and further mixed with an additional 25 mM sodium acetate (pH 4.0) at a flow rate of 9.25 mL/min, to obtain a lipid complex aqueous solution. The obtained lipid complex aqueous solution was subjected to dialysis using a dialysis membrane (trade name "Float-A-Lyzer G2", SPECTRUM Inc., 50K MWCO), and the external solution was replaced with phosphate buffer (PBS, pH7.5). After dialysis, it was concentrated and sterile filtrated, and the composition of Example 10 was obtained.

Example 11

In the same manner as in Example 10 except for using Cationic Lipid 4 of Example 4 instead of Cationic Lipid 1, the composition of Example 11 was obtained.

Example 12

In the same manner as in Example 10 except for using Cationic Lipid 5 of Example 5 instead of Cationic Lipid 1, the composition of Example 12 was obtained.

Example 13

In the same manner as in Example 10 except for using Cationic Lipid 6 of Example 6 instead of Cationic Lipid 1, the composition of Example 13 was obtained.

Example 14

In the same manner as in Example 10 except for using Cationic Lipid 7 of Example 7 instead of Cationic Lipid 1, the composition of Example 14 was obtained.

Example 15

In the same manner as in Example 10 except for using Cationic Lipid 8 of Example 8 instead of Cationic Lipid 1, the composition of Example 15 was obtained.

<Composition Analysis (1)>

Regarding the compositions of Examples 10-15, encapsulation rates of siRNA in the lipid complexes were determined.

Specifically, the composition was diluted with RNase Free Water and siRNA concentration (A) was measured by using Quant-iT RiboGreen RNA Reagent (Invitrogen Corp.). The obtained siRNA concentration (A) was set to the concentration of free siRNA presented in liquid outside of a lipid complex.

Further, the composition was diluted with 1% Triton X-100 and siRNA concentration (B) was measured. The obtained siRNA concentration (B) was set to the total siRNA concentration in the lipid components. Subsequently, encapsulation rate of the nucleic acid was calculated by the following equation (F1):

$$\text{Encapsulation rate (\%)} = 100 - (A/B) \times 100 \tag{F1}$$

Average particle size of lipid complexes was measured by using a particle size measuring apparatus (trade name "Zetasizer Nano ZS", manufactured by Malvern Co.).

Table 1 indicates the encapsulation rate of the siRNA and the average particle size of lipid complexes (Z-average).

TABLE 1

| Composition | Cationic lipid | Encapsulation rate (%) | Average particle size (nm) |
|---|---|---|---|
| Example 10 | 1 | 91 | 64 |
| Example 11 | 4 | 92 | 74 |
| Example 12 | 5 | 94 | 60 |
| Example 13 | 6 | 93 | 62 |
| Example 14 | 7 | 95 | 66 |
| Example 15 | 8 | 96 | 67 |

TABLE 2

| Composition | Cationic lipid | Encapsulation rate (%) | The average particle size (nm) |
|---|---|---|---|
| Example 16 | 2 | 88 | 95 |
| Example 17 | 3 | 94 | 102 |
| Reference Example 14 | 19 | 80 | 87 |
| Reference Example 15 | 21 | 83 | 93 |

Preparation of Composition (2)

Example 16

The composition was prepared by using Cationic Lipid 2 of Example 2. As the nucleic acid, Factor VII siRNA, which was the same as that in the composition of Example 10, was used.

Factor VII siRNA was dissolved in 25 mM sodium acetate (pH 4.0) to produce 538 μg/mL siRNA dilution. In addition, Cationic Lipid 2, DSPC (Nippon Seika Co., Ltd.), Cholesterol (Nippon Seika Co., Ltd.), MPEG2000-DMG (NOF CORPORATION) were dissolved in ethanol in a proportion of 60/8/30/2 (molar ratio) so that the total lipid concentration is 30 mM, to produce a lipid solution. The siRNA diluted solution and the lipid solution were mixed at a flow rate of 2.0 mL/min and 1.08 mL/min, respectively, and further mixed with an additional 25 mM sodium acetate (pH 4.0) at a flow rate of 18.45 mL/min, to obtain a lipid complex aqueous solution. The obtained lipid complex aqueous solution was subjected to dialysis using a dialysis membrane (trade name "Float-A-Lyzer G2", SPECTRUM Inc., 50K MWCO), and the external solution was replaced with phosphate buffer (PBS, pH7.5). After dialysis, it was concentrated and sterile filtrated, and the composition of Example 16 was obtained.

Example 17

In the same manner as in Example 16 except for using Cationic Lipid 3 of Example 3 instead of Cationic Lipid 2, the composition of Example 17 was obtained.

Reference Example 14

In the same manner as in Example 16 except for using Cationic Lipid 19 of Reference Example 10 instead of Cationic Lipid 2, the composition of Reference Example 14 was obtained.

Reference Example 15

In the same manner as in Example 16 except for using Cationic Lipid 21 of Reference Example 12 instead of Cationic Lipid 2, the composition of Reference Example 15 was obtained.

<Composition Analysis (2)>

Regarding the compositions of Examples 16, 17 and Reference Examples 14, 15, encapsulation rates of siRNA in lipid complexes and average particle size were measured in the same manner as the composition of Example 10.

Table 2 indicates the encapsulation rate of siRNA and the average particle size of lipid complexes (Z-average).

Preparation of Composition (3)

Example 18

The composition was prepared by using Cationic Lipid 1 of Example 1. As the nucleic acid, Factor VII siRNA, which was the same as that in the composition of Example 10, was used.

Factor VII siRNA was dissolved in 25 mM sodium acetate (pH 4.0) to produce 400 μg/mL siRNA dilution. In addition, Cationic Lipid 1, DSPC (Nippon Seika Co., Ltd.), Cholesterol (Nippon Seika Co., Ltd.), MPEG2000-DMG (NOF CORPORATION) were dissolved in ethanol in a proportion of 60/8/30/2 (molar ratio) so that the total lipid concentration was 12 mM, to produce a lipid solution. The siRNA diluted solution and the lipid solution were mixed at a flow rate of 2.0 mL/min and 2.0 mL/min, respectively, and further mixed with an additional 25 mM sodium acetate (pH 4.0) at a flow rate of 12.0 mL/min, to obtain a lipid complex aqueous solution. The obtained lipid complex aqueous solution was subjected to dialysis using a dialysis membrane (trade name "Float-A-Lyzer G2", SPECTRUM Inc., 50K MWCO), and the external solution was replaced with phosphate buffer (PBS, pH 7.5). After dialysis, it was concentrated and sterile filtrated, and the composition of Example 18 was obtained.

Example 19

In the same manner as in Example 18 except for using Cationic Lipid 9 of Example 9 instead of Cationic Lipid 1, the composition of Example 19 was obtained.

Reference Example 16

In the same manner as in Example 18 except for using Cationic Lipid 10 of Reference Example 1 instead of Cationic Lipid 1, the composition of Reference Example 16 was obtained.

Reference Example 17

In the same manner as in Example 18 except for using Cationic Lipid 11 of Reference Example 2 instead of Cationic Lipid 1, the composition of Reference Example 17 was obtained.

Reference Example 18

In the same manner as in Example 18 except for using Cationic Lipid 12 of Reference Example 3 instead of Cationic Lipid 1, the composition of Reference Example 18 was obtained.

Reference Example 19

In the same manner as in Example 18 except for using Cationic Lipid 13 of Reference Example 4 instead of Cationic Lipid 1, the composition of Reference Example 19 was obtained.

Reference Example 20

In the same manner as in Example 18 except for using Cationic Lipid 14 of Reference Example 5 instead of Cationic Lipid 1, the composition of Reference Example 20 was obtained.

Reference Example 21

In the same manner as in Example 18 except for using Cationic Lipid 17 of Reference Example 8 instead of Cationic Lipid 1, the composition of Reference Example 21 was obtained.

Reference Example 22

In the same manner as in Example 18 except for using Cationic Lipid 18 of Reference Example 9 instead of Cationic Lipid 1, the composition of Reference Example 22 was obtained.

Reference Example 23

In the same manner as in Example 18 except for using Cationic Lipid 20 of Reference Example 11 instead of Cationic Lipid 1, the composition of Reference Example 23 was obtained.

Reference Example 24

In the same manner as in Example 18 except for using Cationic Lipid 22 of Reference Example 13 instead of Cationic Lipid 1, the composition of Reference Example 24 was obtained.

<Composition Analysis (3)>

Regarding the compositions of Examples 18, 19 and Reference Examples 16-24, encapsulation rates of siRNA in lipid complexes and average particle size were measured in the same manner as the composition of Example 10.

Table 3 indicates the encapsulation rate of siRNA and the average particle size of lipid complexes (Z-average).

TABLE 3

| Composition | Cationic lipid | Encapsulation rate (%) | The average particle size (nm) |
|---|---|---|---|
| Example 18 | 1 | 97 | 92 |
| Example 19 | 9 | 80 | 82 |
| Reference Example 16 | 10 | 90 | 73 |
| Reference Example 17 | 11 | >99 | 105 |
| Reference Example 18 | 12 | 87 | 78 |
| Reference Example 19 | 13 | 88 | 89 |
| Reference Example 20 | 14 | 84 | 83 |
| Reference Example 21 | 17 | 87 | 73 |
| Reference Example 22 | 18 | 82 | 75 |
| Reference Example 23 | 20 | 80 | 81 |
| Reference Example 24 | 22 | 94 | 84 |

Preparation of Composition (4)

Example 20

The composition was prepared by using Cationic Lipid 1 of Example 1. As the nucleic acid, Factor VII siRNA, which was the same as that in the composition Example 10, was used.

The composition of Example 20 was obtained in the same manner as in Example 18.

Comparative Example 1

In the same manner as in Example 20 except for using the compound (hereinafter, refer to ML-5) represented in the following formula (29) described in Patent Document 2 instead of Cationic Lipid 1, the composition of Comparative Example 1 was obtained.

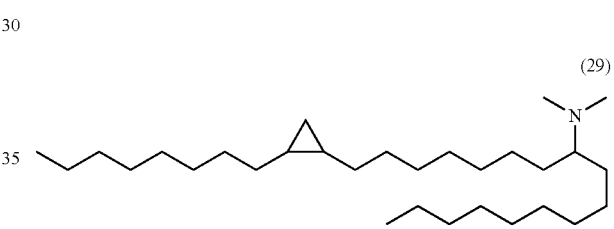

(29)

<Composition Analysis of (4)>

Regarding the compositions of Example 20 and Comparative Example 1, encapsulation rates of siRNA in lipid complexes and the average particle size were measured in the same manner as the composition of Example 10. In addition, the compositions were sealed in vial and stored at 4° C., and encapsulation ratios of siRNA in lipid complexes and the average particle size after one-month storage, two-month storage, four-month storage, six-month storage, nine-month storage, and 12-month storage were measured in the same manner.

Table 4, Table 5, and FIG. 1 indicate time-dependent variation of the encapsulation rate of the siRNA and the average particle size (Z-average) of lipid complexes of Examples 20 and Comparative Example 1, respectively.

TABLE 4

| | Example 20 | | | | | | |
|---|---|---|---|---|---|---|---|
| | 0M | 1M | 2M | 4M | 6M | 9M | 12M |
| Encapsulation rate (%) | 98 | 100 | 100 | 96 | 94 | 97 | 97 |
| Average particle size (nm) | 55 | 57 | 56 | 57 | 62 | 63 | 64 |
| Polydispersity index | 0.11 | 0.12 | 0.12 | 0.13 | 0.09 | 0.11 | 0.09 |

TABLE 5

| | Comparative Example 1 | | | | | | |
|---|---|---|---|---|---|---|---|
| | 0M | 1M | 2M | 4M | 6M | 9M | 12M |
| Encapsulation rate (%) | 98 | 100 | 100 | 97 | 96 | 97 | 98 |
| Average particle size (nm) | 54 | 68 | 73 | 86 | 92 | 112 | 116 |
| Polydispersity index | 0.03 | 0.12 | 0.14 | 0.15 | 0.17 | 0.17 | 0.20 |

It was shown that during storage, increase of particle size of the composition of Example 20 was more suppressed than that of Comparative Example 1.

<Preparation of Composition (5)>

Example 21

The composition was prepared by using Cationic Lipid 1 of Example 1. As the nucleic acid, Factor VII siRNA, which was the same as that in Example 10 composition, was used.

Factor VII siRNA was dissolved in 25 mM sodium acetate (pH 4.0) to produce 108 μg/mL siRNA dilution. In addition, Cationic Lipid 1, DSPC (Nippon Seika Co., Ltd.), Cholesterol (Nippon Seika Co., Ltd.), MPEG2000-DMG (NOF CORPORATION) were dissolved in ethanol in a proportion of 60/8/30/2 (molar ratio) so that the total lipid concentration was 6 mM, to produce a lipid solution. The siRNA diluted solution and the lipid solution were mixed at a flow rate of 3.3 mL/min and 1.81 mL/min, respectively, and further mixed with an additional 25 mM sodium acetate (pH 4.0) at a flow rate of 12.95 mL/min, to obtain a lipid complex aqueous solution. The obtained lipid complex aqueous solutions was subjected to dialysis using dialysis membrane (trade name "Float-A-Lyzer G2", SPECTRUM Inc., 50K MWCO), and the external solution was replaced with phosphate buffer (PBS, p-H7.5)). After dialysis, it was concentrated and sterile filtrated, and the composition of Example 21 was obtained.

Example 22

In the same manner as in Example 21 except for using Cationic Lipid 2 of Example 2 instead of Cationic Lipid 1, the composition of Example 22 was obtained.

Example 23

In the same manner as in Example 21 except for using Cationic Lipid 4 of Example 4 instead of Cationic Lipid 1, the composition of Example 23 was obtained.

Example 24

In the same manner as in Example 21 except for using Cationic Lipid 5 of Example 5 instead of Cationic Lipid 1, the composition of Example 24 was obtained.

Example 25

In the same manner as in Example 21 except for using Cationic Lipid 8 of Example 8 instead of Cationic Lipid 1, the composition of Example 25 was obtained.

Comparative Example 2

As a cationic lipid, except for using above ML-5 instead of Cationic Lipid 1 in the same manner as in Example 21, the composition of Comparative Example 2 was obtained.

<Composition Analysis (5)>

Regarding the compositions of Examples 21-25 and Comparative Example 2, encapsulation rates of siRNA in lipid complexes and the average particle size were measured in the same manner as the composition of Example 10. In addition, the compositions were sealed in vial and stored at 4° C., and encapsulation rates of siRNA in lipid complexes and the average particle size after two-week storage, were measured.

Figure 2:
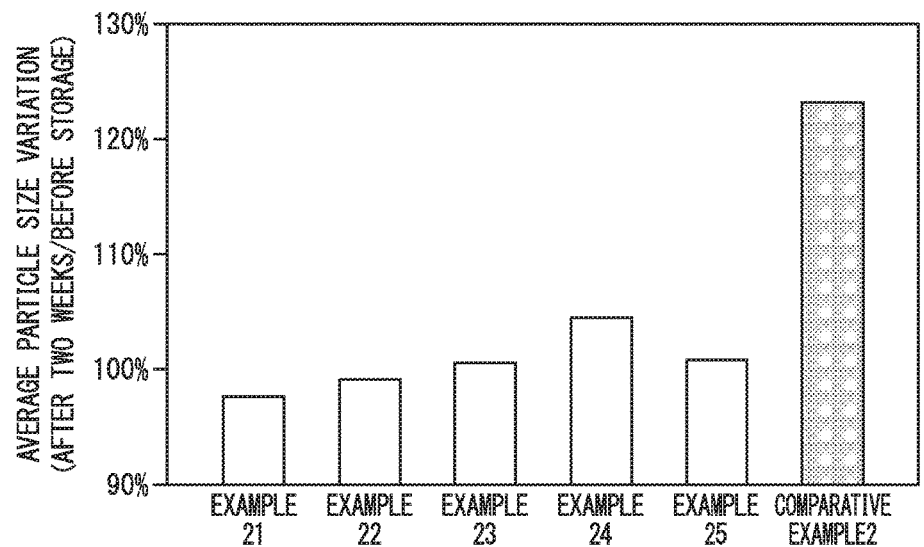
FIG. 2 shows average particle size variation before and after storage of the compositions of Examples 21 to 25 and Comparative Example 2.

Table 6 and FIG. 2 indicate time-dependent variation of average particle sizes (volume average) of the compositions.

TABLE 6

| Composition | Cationic lipid | Before storage | After two weeks | After two weeks/ Before storage (%) |
|---|---|---|---|---|
| Example 21 | 1 | 71 | 69 | 98 |
| Example 22 | 2 | 68 | 67 | 99 |
| Example 23 | 4 | 69 | 69 | 101 |
| Example 24 | 5 | 61 | 64 | 104 |
| Example 25 | 8 | 63 | 64 | 101 |
| Comparative Example 2 | ML-5 | 67 | 83 | 123 |

It was shown that during storage, increase of particle size of the compositions of Examples 21-25 was more suppressed than that of Comparative Example 2.

Evaluation of Composition Activity (1)

Test Example 1

The compositions of Examples 10-15 were diluted with PBS so as to set concentrations of Factor VII siRNA encapsulated in lipid complexes to 10 μg/mL. Each composition was administered to the tail vein of C57/BL6 mice (5-week-old, male) at a dose level of 10 mL/kg, and samples of blood and liver were collected under anesthesia after 24 hours of administration. The plasma was separated from the blood by centrifugation, and then, the concentration of Factor VII protein in the plasma was quantified by a commercially available kit (trade name of "BIOPHEN FVII", HYPHEN BioMed, Inc.). As a negative control, the same treatment was carried out in the group to which PBS was administered.

When setting the Factor VII protein concentration of the PBS administration group to 100%, the Factor VII protein concentrations of the composition administration group were calculated as a relative value. The results are shown in Table 7.

TABLE 7

| siRNA Dose Level (mg/kg) | Composition | Cationic lipid | Factor VII Protein concentration (Relative value) |
|---|---|---|---|
| 0.1 | Example 10 | 1 | 20% |
| | Example 11 | 4 | 32% |
| | Example 12 | 5 | 40% |
| | Example 13 | 6 | 32% |
| | Example 14 | 7 | 18% |
| | Example 15 | 8 | 32% |

The compositions of Examples 10-15 showed a high effect of inhibiting expression of Factor VII protein. That is, it was indicated that according to the cationic lipids of the present invention, the nucleic acids were effectively released into the cytoplasm.

Composition Activity Evaluation of (2)

Test Example 2

The compositions of Examples 16 and 17 and Reference Examples 14, 15 were diluted with PBS so as to set concentrations of Factor VII siRNA encapsulated in lipid complexes to 30 µg/mL. Each composition was administered to the tail vein of C57/BL6 mice (5-week-old, male) at a dose level of 10 mL/kg, and samples of blood and liver were collected under anesthesia after 24 hours of administration. The plasma was separated from the blood by centrifugation, the concentration of Factor VII protein in the plasma was quantified by a commercially available kit (trade name of "BIOPHEN FVII", HYPHEN BioMed, Inc.). As a negative control, the same treatment was carried out in the group to which PBS was administered.

When setting the Factor VII protein concentration of the PBS administration group to 100%, the Factor VII protein concentrations of the composition administration group were calculated as a relative value. The results are shown in Table 8.

TABLE 8

| siRNA Dose Level (mg/kg) | Composition | Cationic lipid | Factor VII Protein concentration (Relative value) |
| --- | --- | --- | --- |
| 0.3 | Example 16 | 2 | 13% |
|  | Example 17 | 3 | 29% |
|  | Reference Example 14 | 19 | 98% |
|  | Reference Example 15 | 21 | 93% |

The compositions of Examples 16 and 17 showed a higher effect of inhibiting expression of Factor VII protein than that of the compositions of Reference Examples 14 and 15. That is, it is indicated that according to the cationic lipids of the present invention, the nucleic acid was effectively released into the cytoplasm.

Composition Activity Evaluation of (3)

Test Example 3

The compositions of Examples 18, 19 and Reference Examples 16-24 were administered to the C57/BL6 mice (5-week-old, male) in the same manner as in Test Example 2. Relative values of Factor VII protein concentrations in plasma and Relative values of the cationic lipid amount remaining in liver after 24 hours of administration were calculated. The results are shown in Table 9.

TABLE 9

| siRNA Dose Level (mg/kg) | Composition | Cationic lipid | Factor VII protein concentration (Relative value) |
| --- | --- | --- | --- |
| 0.3 | Example 18 | 1 | 20% |
|  | Example 19 | 9 | 80% |
|  | Reference Example 16 | 10 | 75% |

TABLE 9-continued

| siRNA Dose Level (mg/kg) | Composition | Cationic lipid | Factor VII protein concentration (Relative value) |
| --- | --- | --- | --- |
|  | Reference Example 17 | 11 | 31% |
|  | Reference Example 18 | 12 | 106% |
|  | Reference Example 19 | 13 | 113% |
|  | Reference Example 20 | 14 | 87% |
|  | Reference Example 21 | 17 | 86% |
|  | Reference Example 22 | 18 | 95% |
|  | Reference Example 23 | 20 | 115% |
|  | Reference Example 24 | 22 | 108% |

The compositions of Example 18 showed a higher effect of inhibiting expression of Factor VII protein than any one of the compositions of Reference Examples 16-24. That is, it is indicated that according to the cationic lipids of the present invention, the nucleic acid was effectively released into the cytoplasm.

From the above results, according to the present invention, it is possible to provide a cationic lipid which is able to efficiently release nucleic acid into the cytoplasm.

Further, according to the present invention, it is possible to provide a cationic lipid which is possible to solve the problem of physical stability such as increases of particle size of lipid complexes during storage for a predetermined period.

The invention claimed is:

1. A cationic lipid which is a compound represented by formula (3) or a pharmaceutically acceptable salt thereof:

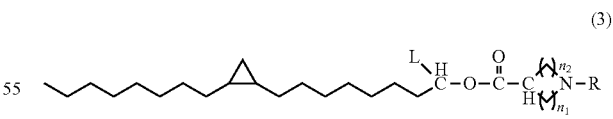

(3)

wherein L is an alkyl having 7-12 carbon atoms or an alkenyl having 7-12 carbon atoms, R is an alkyl having 1-2 carbon atoms, $n_1$ is 2, and $n_2$ is 1.

2. The cationic lipid according to claim 1, wherein the cationic lipid is a compound represented by the following formula (5) or a pharmaceutically acceptable salt thereof:

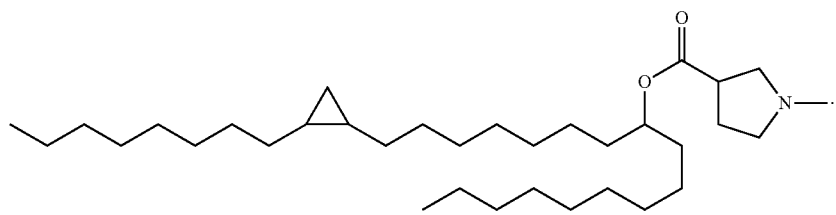
(5)
\* \* \* \* \*